(12) United States Patent
Katakowski et al.

(10) Patent No.: US 10,227,593 B2
(45) Date of Patent: Mar. 12, 2019

(54) METHODS, SYSTEMS, AND COMPOSITIONS FOR CELL-DERIVED/VESICLE-BASED MICRORNA DELIVERY

(71) Applicant: Henry Ford Health System, Detroit, MI (US)

(72) Inventors: Mark E. Katakowski, Ann Arbor, MI (US); Benjamin A. L. Buller, Detroit, MI (US); Michael Chopp, Southfield, MI (US)

(73) Assignee: Henry Ford Health System, Detroit, MI (US)

(*) Notice: Subject to any disclaimer, the term of this patent is extended or adjusted under 35 U.S.C. 154(b) by 0 days.

(21) Appl. No.: 15/390,301

(22) Filed: Dec. 23, 2016

(65) Prior Publication Data

US 2017/0247708 A1    Aug. 31, 2017

Related U.S. Application Data

(63) Continuation-in-part of application No. 14/365,218, filed as application No. PCT/US2012/069419 on Dec. 13, 2012, now Pat. No. 9,555,060.

(60) Provisional application No. 61/570,081, filed on Dec. 13, 2011.

(51) Int. Cl.
| | | |
|---|---|---|
| A61K 48/00 | (2006.01) | |
| C07H 21/02 | (2006.01) | |
| C07H 21/04 | (2006.01) | |
| C12N 15/113 | (2010.01) | |
| A61K 35/28 | (2015.01) | |
| A61K 35/12 | (2015.01) | |

(52) U.S. Cl.
CPC .......... C12N 15/1138 (2013.01); A61K 35/12 (2013.01); A61K 35/28 (2013.01); C12N 15/113 (2013.01); C12N 2310/141 (2013.01); C12N 2320/32 (2013.01)

(58) Field of Classification Search
CPC .......................... A61K 31/713; C12N 15/113
See application file for complete search history.

(56) References Cited

U.S. PATENT DOCUMENTS

| | | |
|---|---|---|
| 9,555,060 B2 | 1/2017 | Katakowski et al. |
| 9,670,490 B2 | 6/2017 | Liu et al. |
| 2006/0235005 A1 | 10/2006 | Goff |
| 2012/0021992 A1 | 1/2012 | Chopp et al. |
| 2017/0321225 A1 | 11/2017 | Liu et al. |

FOREIGN PATENT DOCUMENTS

| | | |
|---|---|---|
| WO | 2007/126386 | 11/2007 |
| WO | 2009/147519 | 12/2009 |
| WO | 2010/119256 | 10/2010 |
| WO | WO 2011/057003 A2 * | 5/2011 ......... C12N 2310/11 |
| WO | WO 2012/044783 A2 | 4/2012 |
| WO | WO 2013/124817 A2 | 8/2013 |

OTHER PUBLICATIONS

PCT International Search Report, PCT/US2012/069419, dated Jul. 11, 2013 (6 pages).
Alvarez-Erviti et al., "Delivery of siRNA to the mouse brain by systemic Injection of targeted exosomes", Nature Biotechnology, 29(4):341-347, 2011.
Baj-Krzyworzeka et al., "Tumour-derived microvesicles carry several surface determinants and mRNA of tumour cells and transfer some of these determinants to monocytes", Cancer Immunol Immonother, 55(7):808-818, 2006.
Galanis et al., "Clinical outcome of gliosarcoma compared with glioblastoma multiforme: North Central Cancer Treatment Group results", J. Neurosurg., 89(3):425-430, 1998 (Abstract).
Katakowski et al., "MiR-146b-5p Suppresses EGFR Expression and Reduces In Vitro Migration and Invasion of Glioma", Cancer Investigation, 28(10):1024-1030, 2010.
Katakowski et al., "Exosomes from marrow stromal cells, expressing miR-146b inhibit glioma growth," Cancer Letters, 335(1):201-204, 2013.
Okada, "Gene Therapy with Vector-producing Multipotent Mesenchymal Stromal Cells", Yakugaku Zasshi, 130(11):1513-1518, 2010.
Parisi et al., "Dysregulated microRNAs in amyotrophic lateral sclerosis microglia modulate genes linked to neuroinflammation", Cell Death and Disease, 4:e959, 2013, pp. 1-10.
Roccaro et al., "Stroma-Derived Exosomes Mediate Oncogenesis in Multiple Myeloma", Blood, 118(21):286, 2011 Abstract 625, 53rd Annual Meeting and Exposition of the American Society of Hematology (ASH); San Diego, CA, USA; Dec. 10-13, 2011.
Valadi et al., "Exosome-mediated transfer of mRNAs and microRNAs is a novel mechanism of genetic exchange between cells", Nature Cell Biology, 9(6):654-659, 2007.
Xia et al., "microRNA-146b inhibits glioma cell migration and invasion by targeting MMPs", Brain Research, 1269:158-165, 2009.
EP Communication, EP 12 809 048.7, dated Aug. 18, 2016 (6 pages).
PCT International Preliminary Report on Patentability (IPRP), PCT/US2012/069419, dated Jun. 14, 2014 (7 pages).
Cogswell J. et al. "Identification of miRNA changes in Alzheimer's disease brain and CSF yields putative biomarkers and insights into disease pathways", Journal of Alzheimer's Disease, vol. 14, No. 1, p. 27-41 2008.

(Continued)

*Primary Examiner* — Amy H Bowman
(74) *Attorney, Agent, or Firm* — Cooley LLP; Ivor R. Elrifi; Matthew Pavao

(57) ABSTRACT

Some embodiments comprise methods, systems, and compositions to produce and/or administer modified exosomes or other vesicles containing one or more selected microRNAs, including but not limited to, miR-146b. Some embodiments also comprise the therapeutic administration and use of such modified exosomes and/or producer cells to treat mammalian brain or neurologic injuries and diseases, including in human beings.

14 Claims, 12 Drawing Sheets

Specification includes a Sequence Listing.

(56) References Cited

OTHER PUBLICATIONS

Maes et al. "MicroRNA: implications for Alzheimer Disease and other human CNS disorders", Current Genomics, vol. 10, No. 3, pp. 154-168 2009.
Wang, Li-Ling et al., "The potential role of microRNA • 146 in Alzheimer's disease: Biomarker or therapeutic target?" Medical Hypotheses, 78:398-401, 2012.

* cited by examiner

METHODS, SYSTEMS, AND COMPOSITIONS FOR CELL-DERIVED/VESICLE-BASED MICRORNA DELIVERY

CROSS-REFERENCE TO RELATED APPLICATIONS

This application is a continuation-in-part of U.S. patent application Ser. No. 14/365,218, filed Jun. 13, 2014, which is a 35 U.S.C. § 371(c) United States National Phase filing of International Patent Application Serial No. PCT/US2012/069419, filed Dec. 13, 2012, which claims the benefit of priority to U.S. Provisional Patent Application Ser. No. 61/570,081, filed Dec. 13, 2011, the entire contents of all of the referenced disclosures are incorporated herein by reference in their entireties.

SEQUENCE LISTING

This application incorporates by reference in its entirety the Sequence Listing entitled "25824-406127_ST25.txt" (14.3 KB), which was created on Mar. 2, 2017.

TECHNICAL FIELD

Without limitation, some embodiments of the invention comprise methods, systems, and compositions relating to microRNAs and the use of same in the research, diagnosis, and treatment of injury or disease.

BACKGROUND

Despite advances in diagnostics, chemotherapeutics, and surgical techniques, the prognosis for certain types of cancers, including but not limited to, brain cancers like glioblastoma multiforme ("GBM"), remains poor.

MicroRNAs ("miRNAs" or "miRs") can regulate gene expression in cells and might be used for therapeutic benefit. As nonlimiting examples, miRNAs can be used to inhibit tumor progression, or to promote tissue healing. Epidermal growth factor receptor ("EGFR") and miR-146b expression have been shown to be inversely correlated in GBMs. However, many EGFR inhibitors have largely failed to induce GBM regression clinically, even where the relationship between genotype and drug response is observed in other cancers. Moreover, GBMs display a variety of genetic aberrations. Thus, a need remains for therapeutic treatments for many cancers, including but not limited to, GBM.

One difficulty that must be overcome for effective miRNA therapy is efficient delivery of the therapeutic miRNAs into the targeted cells, tissues, or organs. A predominant technical challenge in developing a miRNA-based therapy is getting target cells to efficiently absorb and incorporate significant amounts of miRNA.

SUMMARY

The following examples of some embodiments are provided without limiting the invention to only those embodiments described herein and without disclaiming any embodiments or subject matter.

Some embodiments provide methods, systems, and/or compositions using miRNAs which are effectively targeted to, absorbed by, and/or incorporated in cells, tissues, or organs for therapeutic treatments. Some embodiments comprise methods, systems, and/or compositions to produce and/or administer modified exosomes or other vesicles containing one or more selected miRNAs, including but not limited to, miR-146b. In some embodiments, without limitation, miRNA-encoding plasmids are transfected into producer cells, including but not limited to, multipotent mesenchymal stromal cells ("MSCs"). Exosomes containing the transfected miRNAs are harvested from those cells and are used for administration to a subject suffering from injury or illness. Additionally or alternatively, producer cells having miRNA derived from the modified exosomes may be harvested and administered to the subject. Some embodiments comprise the therapeutic administration and use of such miRNAs, modified exosomes, and/or producer cells to treat mammalian injuries and diseases, including in human beings.

In another aspect, some embodiments provide methods, systems, and/or compositions for treating a subject suffering from a neurological disease or injury with exosomes containing miR-146b microRNA, comprising the steps of: (a) harvesting exosomes containing miR-146b microRNA from a cell population capable of producing exosomes containing miR-146b microRNA or media containing the cell population, (b) confirming the presence of the miR-146b microRNA in the harvested exosomes; and (c) administering to the subject in need thereof, the harvested exosomes in a pharmaceutically effective amount to treat the subject with the neurological disease or injury.

In another related aspect, some embodiments provide methods, systems, and/or compositions for treating a subject suffering from a neurological disease or injury with cells capable of producing miR-146b microRNA, the method comprising: (a) providing a cell population capable of producing exosomes containing miR-146b; (b) confirming the presence of the miR-146b microRNA in the cell population, and (c) administering to the subject in need thereof the cell population capable of producing exosomes containing miR-146b microRNA in a pharmaceutically effective amount to treat the subject with respect to the neurological disease or injury.

BRIEF DESCRIPTION OF THE DRAWINGS

Some embodiments will now be described, by way of example only and without disclaimer of other embodiments, with reference to the accompanying drawings, in which:

DETAILED DESCRIPTION

Figure 1:
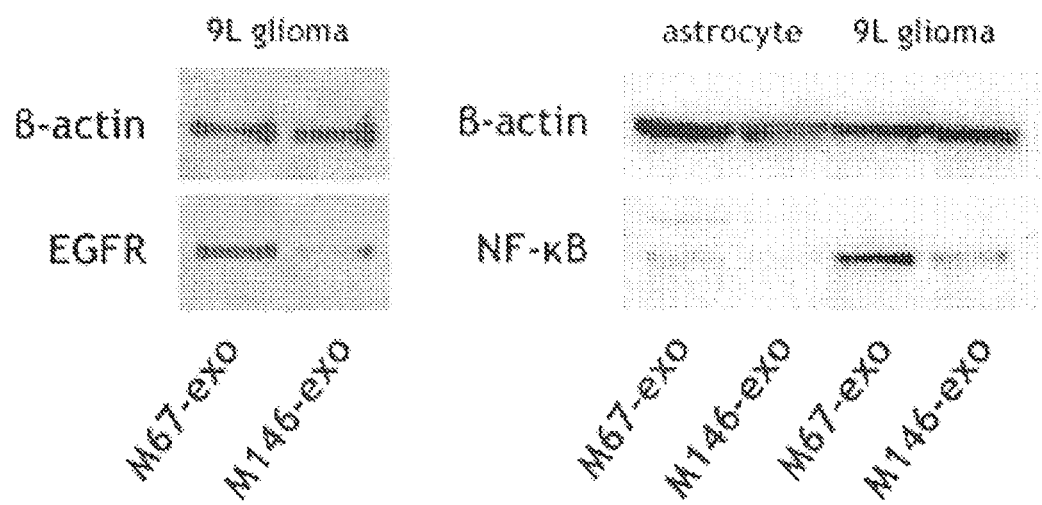
FIG. 1 is a data representation and images showing that exosomes from MSCs transfected with a miR-146b expression plasmid reduce EGFR and NF-κB when administered to cultures of 9 L glioma cells.

Without limitation to only those embodiments expressly disclosed herein and without disclaiming any embodiments or subject matter, some embodiments comprise a miRNA delivery system whereby miRNA expression is modified in target exosome-producing cells (as one nonlimiting example, MSCs), and exosomes or other vesicles, miRNAs from those cells, and/or those cells themselves, are used as delivery vehicles to deliver therapeutic miRNA(s) into cells, tissue, or organs. Some embodiments comprise the therapeutic administration and use of such induced cells to treat mammalian injuries and diseases, including but not limited to, nervous system injuries or diseases that may otherwise result in decreased cell or system function. In some embodiments, such induction of differentiated MSCs, and/or the resulting cells, may be used to treat cell, tissue, or organ damage in a patient by administering to said patient a therapeutically effective amount of a miRNA of interest, or of differentiated MSCs induced by such miRNAs.

A pressing problem in treatment with miRNA is getting target cells to efficiently absorb and incorporate the miRNA. Some embodiments will effectively deliver therapeutic miRNAs to tissue or other locations within a subject for treatment. For example, certain embodiments could be used to produce custom exosomes that carry one or more species of anti-tumor miRNAs that could be administered to a cancer patient. Alternately, certain embodiments could be used to produce custom exosomes that carry one or more species of neuro-restorative miRNAs that could be administered to a stroke patient. Some embodiments comprise a customizable miRNA delivery system that could be used to treat multiple pathologies in whose treatment miRNA therapy would be useful.

MiRNAs can regulate gene expression in cells, and can be used for therapeutic benefit. For example, miRNAs can be used to inhibit tumor progression, or to promote tissue healing. One difficulty that must be overcome for effective miRNA therapy is efficient delivery of the miRNA(s) to the affected cell, tissues or organs.

Some embodiments comprise the packaging of exosomes with one or more species of miRNA, and as the miRNA can be endogenous to the producing cell, or foreign, or artificially designed (as only one example, by original DNA plasmid(s) design), they comprise a versatile method of miRNA delivery. For example, whereas many nucleotide delivery vehicles such as liposomes or nanoparticles require preloading or binding the vehicle with the nucleotide, certain embodiments use the producer cells to create the miRNA and to load the exosome.

Introducing foreign particles into a patient can result in an immune response. In certain embodiments, if cells such as MSCs are used, it is possible to use the patient's own MSCs as producer cells; therefore, it is likely that immune rejection of the delivery vehicles could be circumvented or reduced.

Without limitation, some embodiments comprise ongoing production of miRNA-bearing exosomes, and also enable transplantation of miRNA-bearing exosome producing cells. Once transfected, producer cells could create or continue to produce custom miRNA-bearing exosomes and miRNAs for an extended period of time. The miRNA may comprise the entire sequence of the miRNA, or it may comprise any subfragment or variant thereof which retains the targeted activity of the entire sequence. This creation or production could provide certain advantages, including but not limited to: 1) exosomes could be harvested at many time points and delivered to the patient over many days or weeks, and 2) the producer cells themselves might be transplanted into the tissue to be treated to produce custom miRNA-bearing exosomes and miRNAs on site.

We have discovered that miRNAs that are introduced into MSCs, and certain other cell types, are subsequently released from the cells in exosomes. As a nonlimiting example, when we transfected MSCs with a DNA plasmid that encoded the *C. elegans* miRNA cel-miR-67, we found an abundance of cel-miR-67 miRNA in the exosomes released from these MSCs. As exosomes can be incorporated in other cells, we have invented, in some embodiments, a miRNA production and delivery system whereby miRNA expression is modified in target exosome-producing cells (as one nonlimiting example, MSCs), and exosomes from those cells, and/or the cells themselves, are used as delivery vehicles to take therapeutic miRNA(s) into cells, tissue, or organs.

In some embodiments, we transfected producer cells (MSCs, 9 L glioma cells and HEK cells) with DNA plasmids that are designed to encode for miRNAs. In some embodiments, we used plasmids that encoded for cel-miR-67 (a control miRNA not found in mammalian cells), and miR-146b (a miRNA that we previously found had anti-tumor effects). We harvested exosomes produced from these cells (after 1 day, 2 days and 3 days), and using RT-PCR, we detected cel-miR-67 only in exosomes from cells that were transfected with the cel-miR-67 plasmid. Furthermore, we detected highly elevated levels (up to 160× control) of miR-146b in the exosomes that were transfected with the miR-146b plasmid. Based on our other work, treating glioma cells with cel-miR-67 would have no effect upon cell viability, whereas treating glioma cells with miR-146b would reduce cell viability and reduce tumor cell invasion. Deletions on chromosome 10 are the most frequent chromosomal alteration observed in GBMs, with approximately 80% of cases exhibiting loss of heterozygosity. Human miR-146b is located on chromosome 10 within 10q24-26, a region most frequently lost in GBM. We found that U87-MG, U251 and cells, and HFH66 primary human glioblastoma cells, express significantly less miR-146b than normal cortical human astrocytes. EGFR gene amplification occurs in approximately 40% of all GBMs and increased EGFR expression correlates with glioma invasiveness and malignancy. The EGFR signaling network has been a target for anti-tumor therapy, with significant effort focused on inhibiting the receptor using antibodies, tyrosine kinase inhibitors, or vaccines.

In our work, we treated 9 L gliosarcoma cells with exosomes from cel-miR-67 plasmid-transfected cells and miR-146b plasmid-transfected cells, as well as exosomes from non-transfected cells. Using MTT we found that glioma cell viability was significantly reduced when treated with exosomes from miR-146b plasmid transfected cells compared to all controls. Therefore, using a miR-146b plasmid and producer cells, we effectively and efficiently administered miR-146b to tumor cells, eliciting a significant anti-tumor effect.

MiRNAs inhibit translation of their target mRNAs. MiR-146b can inhibit production of certain tumor promoting proteins, among them, EGFR, NF-κB, IRAK1 and TRAF6. Using Western blot, we have found that exosomes from cells transfected with miR-146b plasmid significantly reduced EGFR, NF-κB, IRAK-1, and TRAF6 expression in glioma cells compared to cells treated with control exosomes or exosomes from cel-miR-67 plasmid transfected cells. Other proteins that are targets of miR-146b in other systems were unaffected, such as MMP16, indicating that the effect we observed was specific. FIG. 1 shows protein expression in glioma cells and astrocytes after exposure to MSC exosomes. As indicated, miR-146b exosomes ("M146-exo") reduced EGFR and NF-κB protein expression in 9 L cells compared to cel-miR-67 exosomes ("M67-exo"). NF-κB M146-exo also slightly reduced NF-κB protein in primary cortical rat astrocytes. These results show that miR-146b packaged in exosomes could significantly inhibit its targeted proteins in treated tumor cells but not non-tumor astrocytes.

Some embodiments comprise a novel and versatile miRNA delivery system which can be applied in a wide range of diseases or injuries. Using some embodiments clinically, anti-tumor miRNAs could be packaged in exosomes, and these exosomes could be administered to the subject. The ability to efficiently package one or more species of miRNAs of some embodiments results in a versatile miRNA delivery system. Thus, depending upon the miRNAs that are packaged, a wide range of diseases or injuries could be treated with modified exosomes comprising some embodiments.

Furthermore, as described herein, producer cells could be administered to a targeted location in a subject, resulting in local sustained production of custom miRNA bearing exosomes, and/or the therapeutic release of selected miRNAs from the producer cells themselves.

Certain embodiments comprise features which include, but are not limited to: 1) an effective method of miRNA delivery as cell derived vesicles are easily incorporated into cells, 2) production of cell derived vesicles (as one nonlimiting example, exosomes) that can contain one or more species of miRNA, and these can be endogenously occurring, or custom designed miRNAs, 3) as any miRNA(s) can be packaged, production of miRNA-bearing exosomes for treatment of many different diseases, 4) use of exosome-producing cells for an ongoing supply of ex vivo miRNA-bearing exosomes, and/or transplantation in vivo to locally produce miRNA-bearing exosomes, 5) use of multiple cell types to produce miRNA-bearing exosomes, 6) use of modified cells and/or exosomes designed to specifically target tissues of therapeutic interest, and 7) avoidance or mitigation of adverse effects, as exosomes are naturally occurring and thus custom miRNA bearing exosomes will likely have few adverse effects when administered.

Some embodiments may comprise the production and/or administration of other similarly modified, cell-derived membrane vesicles in addition to or concurrently with modified exosomes.

Figure 2:
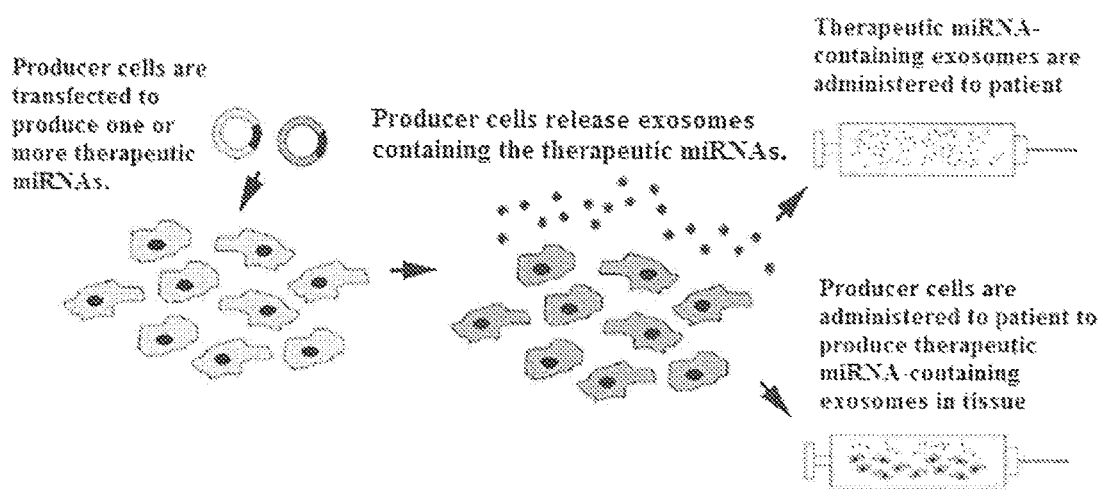
FIG. 2 shows an overview of an exosome-based therapeutic miRNA delivery system.

Certain embodiments comprise methods, systems, and/or compositions to deliver therapeutic miRNA molecules into tissue of patients. As illustrated in FIG. 2, some embodiments comprise methods and/or systems with one or more of the following steps: 1) MiRNAs that have been determined to be therapeutic are expressed in exosome producing cells, 2) the producing cells begin to release exosomes that contain the introduced therapeutic miRNAs, and 3) therapeutic miRNA-containing exosomes are harvested and administered to the patient, and/or producing cells are administered to the patient to release therapeutic miRNA-containing exosomes after administration.

Some embodiments comprise the packaging of exosomes with one or more species of miRNA at high concentrations, and these miRNAs are delivered into tissue in therapeutic doses. Packaged miRNAs can be those that are endogenous to the producing cells, but are forced to express at higher levels, or may be artificially designed miRNAs, introduced to suit the therapeutic need. Also, a combination of miRNAs can be packaged within the same exosomes.

In various embodiments, the present invention provides a method of treating a subject or patient suffering from a neurological disease or injury. The treatment comprises treating the patient in need thereof, with exosomes containing miR-146b microRNA. The method comprises the steps of: harvesting exosomes containing miR-146b microRNA from a cell population capable of producing exosomes containing miR-146b microRNA or media containing the cell population, confirming the presence of the miR-146b microRNA in the harvested exosomes; and administering to the subject or patient in need thereof, the harvested exosomes in a pharmaceutically effective amount to treat the subject with the neurological disease or injury.

In other embodiments, the present invention provides a method of treating a subject or patient suffering from a neurological disease or injury. The treatment comprises treating the patient in need thereof, with cells that are capable of producing exosomes containing miR-146b microRNA. The method comprises the steps of: providing a cell population capable of producing exosomes containing miR-146b; confirming the presence of the miR-146b microRNA in the cell population, and administering to the subject in need thereof the cell population capable of producing exosomes containing miR-146b microRNA in a pharmaceutically effective amount to treat the subject with respect to the neurological disease or injury.

In some of these embodiments, the cells that are capable of producing exosomes containing miR-146b microRNA can include: stem cells, mesenchymal stromal cells, umbilical cord cells, endothelial cells, Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia, or mastocytes. As used herein, stem cells, for example, from a human mammalian subject can include, without limitation, a progenitor cell, a pluripotent stem cell, an induced pluripotent stem cell, a hair follicle stem cell, a hematopoietic stem cell, a very small embryonic like stem cell, a mesenchymal stem cell, an endometrial regenerative cell (ERC), or a progenitor cell. In various embodiments, the cell population includes mesenchymal stem cells, and mesenchymal stromal cells.

In various embodiments, methods of the present invention may utilize the above referenced cell populations that are derived from the subject to be treated, or they may be derived from a member of the same species, for example, the cells may be allogeneic.

In various embodiments, the exosomes may be administered to the patient in need thereof intravenously, nasally, intradermally, intraarterially, intraperitoneally, intralesionally, intracranially, intraarticularly, intraprostaticaly, intrapleurally, intratracheally, intravitreally, intravaginally, intrarectally, topically, intratumorally, intramuscularly, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, or stereotactically into neural tissue. In each of these administration modes, the exosomes or cell populations are administered to the subject in need thereof in accordance with standard medically approved methods.

In each of these embodiments, the exosomes may be administered in therapeutically effective amounts. The therapeutically effective amount of exosomes containing the miR-146b microRNA may be dependent on several factors known to those skilled in the art. The amount must be effective to achieve improvement, including but not limited to, decreased damage or injury, or improvement or elimination of one or more symptoms and other indicators as are selected as appropriate measures by those skilled in the art. In some embodiments, neural diseases and injuries that are beneficially treated, and/or prevented upon treatment with effective amounts of exosomes comprising miR146b or cell population bearing exosomes comprising miR146b include, but are not limited to: stroke, brain injury, central pontine, dementia, multiple sclerosis (MS) (together with the similar diseases called idiopathic inflammatory demyelinating diseases), tumefactive multiple sclerosis, Solitary sclerosis, cognitive decline from aging, Alzheimer's disease, Parkinson's disease, epilepsy, migraine, neuropathy, for example, peripheral neuropathy, Vitamin B12 deficiency, myelinolysis, Tabes Dorsalis, transverse myelitis, Devic's neuromyelitis optica, fulminant or acute idiopathic inflammatory-demyelinating disease, Marburg variant of multiple sclerosis, Baló's concentric sclerosis, Schilder's disease, acute disseminated encephalomyelitis; transverse myelitis, optic neuritis, progressive multifocal leukoencephalopathy, acute hemorrhagic leukoencephalitis, acute disseminated encephalomyelitis, anti-myelin oligodendrocyte glycoprotein autoimmune encephalomyelitis, Leukodystrophy, adrenoleukodystrophy, adrenomyeloneuropathy, chronic inflammatory demyelinating polyradiculoneuropathy (CIDP), Guillain-Barre syndrome, chronic inflammatory demyelinating polyneuropathy, or anti-MAG peripheral neuropathy.

In some embodiments, the present invention provides a method of treating a subject suffering from dementia, neuropathy, stroke or multiple sclerosis with exosomes containing miR-146b microRNA. In these exemplary methods, the steps may include: (a) harvesting exosomes containing miR-146b microRNA from a cell population capable of producing the exosomes or media containing the cell population, (b) confirming the presence of the miR-146b microRNA in the harvested exosomes, and (c) administering to the subject in need thereof, the harvested exosomes containing miR-146b microRNA in a pharmaceutically effective amount to treat the subject with the dementia, neuropathy, stroke or multiple sclerosis. In each of these exemplary methods, the exosome producing cell population may include stem cells, mesenchymal stromal cells, umbilical cord cells, endothelial cells, Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia; or mastocytes. As used herein, stem cells may include, a progenitor cell; a pluripotent stem cell; an induced pluripotent stem cell; a hair follicle stem cell; a hematopoietic stem cell; a very small embryonic like stem cell; a mesenchymal stem cell; an endometrial regenerative cell (ERC); or a progenitor cell.

In these methods, the cells used to dementia, neuropathy, stroke or multiple sclerosis with exosomes containing miR-146b microRNA the exosomes containing the miR-146b may be obtained from autologous cell populations. In various embodiments of the above referenced methods of treatment of dementia, neuropathy, stroke or multiple sclerosis with exosomes containing miR-146b microRNA, the exosomes may be administered intravenously, nasally, intradermally, intraarterially, intraperitoneally, intralesionally, intracranially, intraarticularly, intraprostaticaly, intrapleurally, intratracheally, intravitreally, intravaginally, intrarectally, topically, intratumorally, intramuscularly, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, or directly into neural tissue.

As used herein, it is believed that the oxygen deprivation (ischemia) and inflammation of the brain lead to several neurological diseases and injuries which may be chronic and/or acute. In some embodiments, neurological inflammation can progress to demyelination of neurons. Demyelination is the act of demyelinating, or the loss of the myelin sheath insulating the nerves. When myelin degrades, conduction of signals along the nerve can be impaired or lost, and the nerve eventually withers. This leads to certain neurodegenerative disorders like multiple sclerosis and chronic inflammatory demyelinating polyneuropathy. Central nervous system (CNS) demyelination is a cause and consequence of a variety of neurological diseases and especially exemplified by MS and cognitive decline from aging, which follow a relapsing-remitting but then progressive course and a more protracted but progressive course, respectively. In both instances, these maladies involve increased oxidative stress (OS), which damages brain cells of oligodendrocyte lineage that are responsible for brain myelination, and production of myelination inhibitory factors including specific miRNAs.

According to an embodiment of the invention, the methods described herein are useful in inhibiting the development of and/or treating multiple sclerosis. Multiple sclerosis (MS), also known as "disseminated sclerosis" or "encephalomyelitis disseminata", is an inflammatory disease in which the fatty myelin sheaths around the axons of the brain and spinal cord are damaged, leading to demyelination and scarring as well as a broad spectrum of signs and symptoms. Disease onset usually occurs in young adults, and it is more common in women. It has a prevalence that ranges between 2 and 150 per 100,000.

Demyelination may also play an important role in the pathophysiology of traumatic brain injury. In experimental studies, brain injuries have been shown to be accompanied by a loss of myelin.

Neonatal brain disorders are also associated with demyelination and failure of remyelination. White matter injuries in the newborn brain, such as hypoxic ischemic encephalopathy and periventricular leukomalacia can result in cerebral palsy and cognitive disability. Failure of remyelination in such conditions contributes to permanent demyelinated lesions. Methods of the present invention are provided to treat, ameliorate and diminish any of the symptoms of ischemic tissue injury in the brain and the demyelination associated with brain diseases, disorders described above and below.

The present invention provides a method of treating or preventing a neurological disease or injury. In some embodiments, the neurological disease or injury is a disease or injury that results from direct trauma to the brain, an acute or chronic autoimmune insult, or an acute or chronic inflammation, either systemically, or locally in the brain. In some embodiments, the neurological disease or injury is treated upon administration of a therapeutically effective amount of exosomes containing miR-146b or cells from a cell population capable of producing exosomes containing miR-146b. In some of these embodiments, said patient is administered a therapeutically effective amount of exosomes containing miR-146b microRNA or cells from a cell population capable of producing exosomes containing miR-146b microRNA of the invention conjointly with an immune system suppressor, and/or an anti-inflammatory agent, for example, a glucocorticoid.

Exosomes containing miR-146b or cells from a cell population capable of producing exosomes containing miR-146b of the invention are capable of resolving, diminishing, ameliorating or improving a symptom associated with inflammation occurring in the brain of the subject, preferably a human subject. Glucocorticoids are also known for their role in treating inflammation. However, the full anti-inflammatory potential of glucocorticoids is often clinically constrained as a monotherapy due to the rate and severity of treatment-limiting adverse events that accompany high or prolonged dosing regimens. For example, the administration of glucocorticoids can result in side effects that mimic Cushing's disease. These side effects and others associated with glucocorticoid use include increased appetite and weight gain, deposits of fat in the chest, face, upper back, and stomach, water and salt retention leading to swelling and edema, high blood pressure, diabetes, slow healing of wounds, osteoporosis, cataracts, acne, muscle weakness, thinning of the skin, increased susceptibility to infection, stomach ulcers, increased sweating, mood swings, psychological problems such as depression, and adrenal suppression and crisis. Advantageously, treatment of a subject in need thereof having a neurologic disease or injury with a combination of a glucocorticoid and exosomes containing miR-146b or cells from a cell population capable of producing exosomes containing miR-146b of the invention enhances the anti-inflammatory properties of both classes of agents while reducing the effects associated with high doses of glucocorticoids alone.

In methods of the invention, wherein a glucocorticoid is administered conjointly with exosomes containing miR-146b or cells from a cell population capable of producing exosomes containing miR-146b of the invention, the glucocorticoid may be chosen from any glucocorticoid known in the art. Glucocorticoids suitable for said conjoint administration include, but are not limited to, alclometasone, amcinonide, beclometasone, betamethasone, budesonide, ciclesonide, clobetasol, clobetasone, clocortolone, cloprednol, cortisone, cortivazol, deflazacort, desonide, desoximetasone, desoxycortone, dexamethasone, diflorasone, diflucortolone, difluprednate, fluclorolone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, prednylidene, rimexolone, tixocortol, triamcinolone, ulobetasol, mometasone, fluticasone propionate, beclomethasone dipropionate, fluocinolone, flunisolide hemihydrate, mometasone furoate monohydrate, desoxymethasone, diflorasone diacetate, hydrocortisone acetate, difluorocortolone, fluorocortisone, flumethasone, flunisolide, fluorocortolone, prednisolone, prednisone, cortisol, 6a-methylprednisolone, alclometasone dipropionate, fluclorolone acetonide, fluocinolone acetonide, betamethasone benzoate, fluocoritin butyl, betamethasone dipropionate, fluocortolone preparations, betamethasone valerate, fluprednidene acetate, flurandrenolone, clobetasol propionate, clobetasol butyrate, hydrocortisone, hydrocortisone butyrate, methylprednisolone acetate, diflucortolone valerate, flumethasone pivalate, or triamcinolone acetonide, or pharmaceutically acceptable salts thereof.

In certain embodiments, the patient to be treated by a method of the invention may already be receiving an anti-inflammatory drug (other than a glucocorticoid). In one preferred embodiment, the patient is already taking a glucocorticoid, such as one of the glucocorticoids described above, and will continue to take that drug conjointly with a composition comprising exosomes containing miR-146b or cells from a cell population capable of producing exosomes containing miR-146b of the invention. Alternatively, the exosomes containing miR-146b or cells from a cell population capable of producing exosomes containing miR-146b of the invention may be used as a replacement for the previously administered anti-inflammatory, anti-autoimmune or immune suppressing drug, for example, an anti-CD40 L antibody, methotrexate, hydrocortisone, prednisone, prednisolone, methylprednisolone, betamethasone, VERIPRED™ ORAPRED™, triamcinolone acetonide, AVONEX™ (interferon beta-1a), BETASERON™ (interferon beta-1b), COPAXONE™ (glatiramer acetate), EXTAVIA™ (interferon beta-1b), GLATOPA™ (glatiramer acetate (Copaxone 20 mg dose)), PLEGRIDY™ (peginterferon beta-1a), REBIF™ (interferon beta-1a), ZINBRYTA™ (daclizumab) AUBAGIO™ (teriflunomide), GILENYA™ (fingolimod), AMPYRA® (Dalfampridine), TECFIDERA™ (dimethyl fumarate), LEMTRADA™ (alemtuzumab), NOVANTRONE™ (mitoxantrone), or TYSABRI™ (natalizumab), or alternatively, all of these anti-inflammatory, anti-autoimmune or immune suppressing drugs may be co-administered individually or in combination with a composition comprising exosomes containing miR-146b microRNA or cells from a cell population capable of producing exosomes containing miR-146b microRNA of the invention, either concurrently or sequentially to treat the neurologic disease or injury as exemplified herein.

In one embodiment, the method of treating or preventing a neurologic disease or injury according to this invention may comprise the additional step of conjointly administering to the patient another anti-inflammatory agent, such as, for example, a non-steroidal anti-inflammatory drug (NSAID), a mast cell stabilizer, or a leukotriene modifier.

In certain embodiments, the use of a composition comprising exosomes containing miR-146b or cells from a cell population capable of producing exosomes containing miR- 146b of the invention and a glucocorticoid or other anti0-inflammatory agent in the treatment of a neurologic disease or injury does not preclude the separate but conjoint administration of another anti-inflammatory agent for example, a corticosteroid, a non-steroidal anti-inflammatory drug (NSAID), a mast cell stabilizer, or a leukotriene modifier.

In certain embodiments, the present invention provides a kit comprising: a) one or more single dosage forms of a composition containing exosomes containing miR-146b or cells from a cell population capable of producing exosomes containing miR-146b of the invention; and b) instructions for the administration of the exosomes containing miR-146b or cells from a cell population capable of producing exosomes containing miR-146b of the invention.

The present invention provides a kit comprising: a) a pharmaceutical formulation (e.g., one or more single dosage forms) comprising exosomes containing miR-146b or cells from a cell population capable of producing exosomes containing miR-146b of the invention; and b) instructions for the administration of the pharmaceutical formulation e.g., for treating or preventing a disorder or condition as discussed above, e.g., a neurologic disease or injury.

In certain embodiments, the kit further comprises instructions for the administration of the pharmaceutical formulation comprising exosomes containing miR-146b or cells from a cell population capable of producing exosomes containing miR-146b of the invention conjointly with a another immune system modulator, an anti-inflammatory agent, for example a corticosteroid, a non-steroidal anti-inflammatory drug (NSAID), a mast cell stabilizer, or a leukotriene modifier or combinations thereof as mentioned above. In certain embodiments, the kit further comprises a second pharmaceutical formulation (e.g., as one or more single dosage forms) comprising an immune system modulator, an anti-inflammatory agent, for example a corticosteroid, a non-steroidal anti-inflammatory drug (NSAID), a mast cell stabilizer, a leukotriene modifier, or a combinations thereof as mentioned above.

EXAMPLES

The following examples of some embodiments are provided without limiting the invention to only those embodiments described herein and without disclaiming any embodiments.

Example 1

Figure 3:
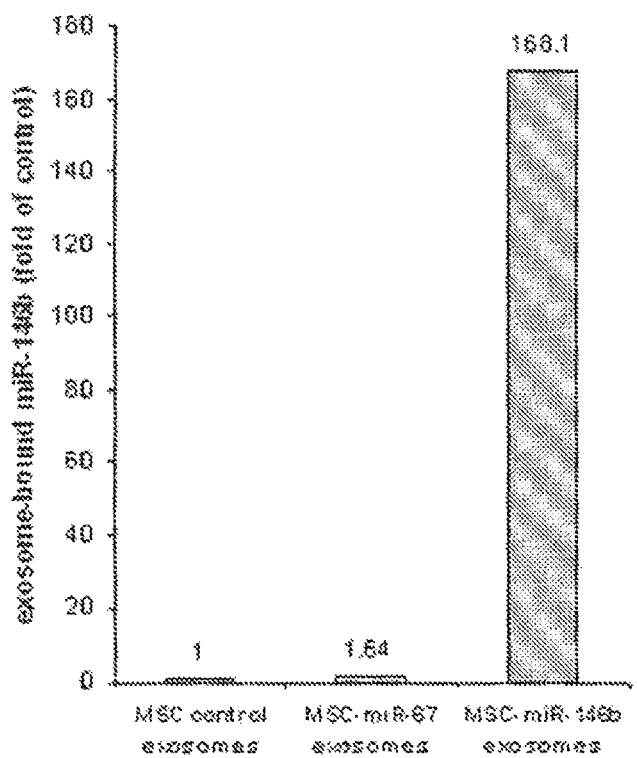
FIG. 3 is a data representation showing that exosomes from MSCs transfected with a miR-146b expression plasmid release exosomes that contain significantly higher levels of miR-146b.

We have found that miRNAs that are introduced into MSCs or other cells are subsequently packaged in exosomes in abundance, and released from the cells. These exosomes containing introduced miRNAs can then be isolated from the culture medium. For example, when we transfected MSCs with a DNA plasmid that encoded miRNA cel-miR-67, we found an abundance of cel-miR-67 miRNA in the exosomes released from these MSCs. MiRNA cel-miR-67 is not naturally produced by mammalian MSCs. Therefore in some embodiments, one can package non-native miRNAs into exosomes, which means that some embodiments might be used to design small miRNA-like sequences that are customized to target any gene of interest. We also found unexpectedly that when MSC cells were transfected with rno-miR-146b, a miRNA native to mammalian MSCs, exosomes from miR-146b-transfected MSCs contained significantly higher levels of miR-146b compared to control (FIG. 3). We detected miR-146b levels to be relatively higher in exosomes from miR-146b producing cells compared to exosomes from naive cells, than the miR-146b levels in the cell bodies of the respective groups. Furthermore, the levels of miR-146b detected in MSC exosomes from miR-146b producing cells was consistently and unexpectedly increased to levels several fold higher than that of cel-miR-67 detected in exosomes from cel-miR-67 producing cells, even when normalized for naive levels of miR-146b in MSC exosomes. These data indicate that miR-146b is preferentially packaged into exosomes by the producer cells. As per above, exosomes can also be collected from certain other cell types, such as 9 L, HEK, astrocytes, or oligodendrocytes. However, we found these certain other cell types lack the production capacity of MSCs, and as such, when transfected in accordance with some embodiments, MSCs are a novel and highly efficient producer cell. In addition, we found that miR-146b expression did not compromise production of exosomes by MSCs or significantly alter the viability of the MSCs, a key feature, as some anti-tumor miRNAs can suppress metabolic processes in cells. As exosomes can be incorporated in other cells, in some embodiments, we have developed the use of MSC exosomes as a delivery vehicle for therapeutic miRNAs.

Example 2

A current problem for treatment with therapeutic miRNA is getting the target cells to efficiently absorb and incorporate the miRNA. Some embodiments use exosomes that are easily absorbed from cells such as MSCs. We then package therapeutic miRNA or a combination of therapeutic miRNAs into MSC exosomes, and employ the exosomes as the delivery vehicle. For example, some embodiments could be used to produce custom exosomes that carry one or more species of anti-tumor miRNAs that could be administered to the cancer patient. Alternately, some embodiments could be used to produce custom exosomes that carry neuro-restorative miRNAs to be administered to a patient suffering from a neurological disease such as Alzheimer's disease, or stroke. Some embodiments comprise a customizable miRNA delivery system that could be used to treat multiple pathologies in which treatment with miRNA therapy would be useful.

Figure 4:
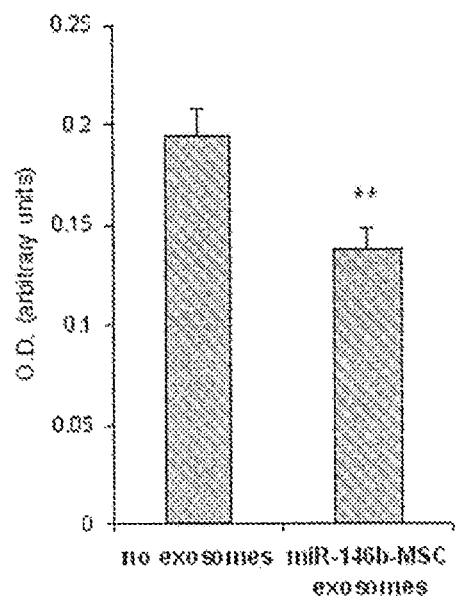
FIG. 4 is a data representation showing that exosomes from MSCs transfected with a miR-146b expression plasmid release exosomes that decrease viability of 9 L gliosarcoma tumor cells.

We have packaged the anti-tumor miRNA miR-146b in MSC exosomes and treated 9 L gliosarcoma cells with these exosomes in vitro. Using the MTT cell viability assay, we found that 9 L gliosarcoma cell viability was significantly reduced when treated with miR-146b-containing MSC exosomes compared to control (FIG. 4, showing that exosomes from MSCs transfected with a miR-146b expression plasmid release exosomes that decrease cell viability of 9 L gliosarcoma tumor cells.). Therefore, using a miR-146b plasmid and producer cells to package miR-146b in MSC exosomes, we effectively and efficiently administered miR-146b to tumor cells, eliciting a significant anti-tumor effect. To determine whether MSC exosomes carrying miR-146b deliver the miRNA into tumor cells, we exposed 9 L cells to miR-146b-containing MSC exosomes (M146-exo) or cel-miR-67-containing exosomes (M67-exo) in vitro. After 24 hours treatment, miR-146b detected in M146-exo-treated 9 L cells was 8.5±0.4 times higher compared to M67-exo-treated cells, whereas cel-miR-67 was detected in M67-exo-treated 9 L cells, but not detected M146-exo-treated cells. This indicated that MSC exosomes can deliver plasmid-expressed miRNAs into tumor cells.

Example 3

Figure 5:
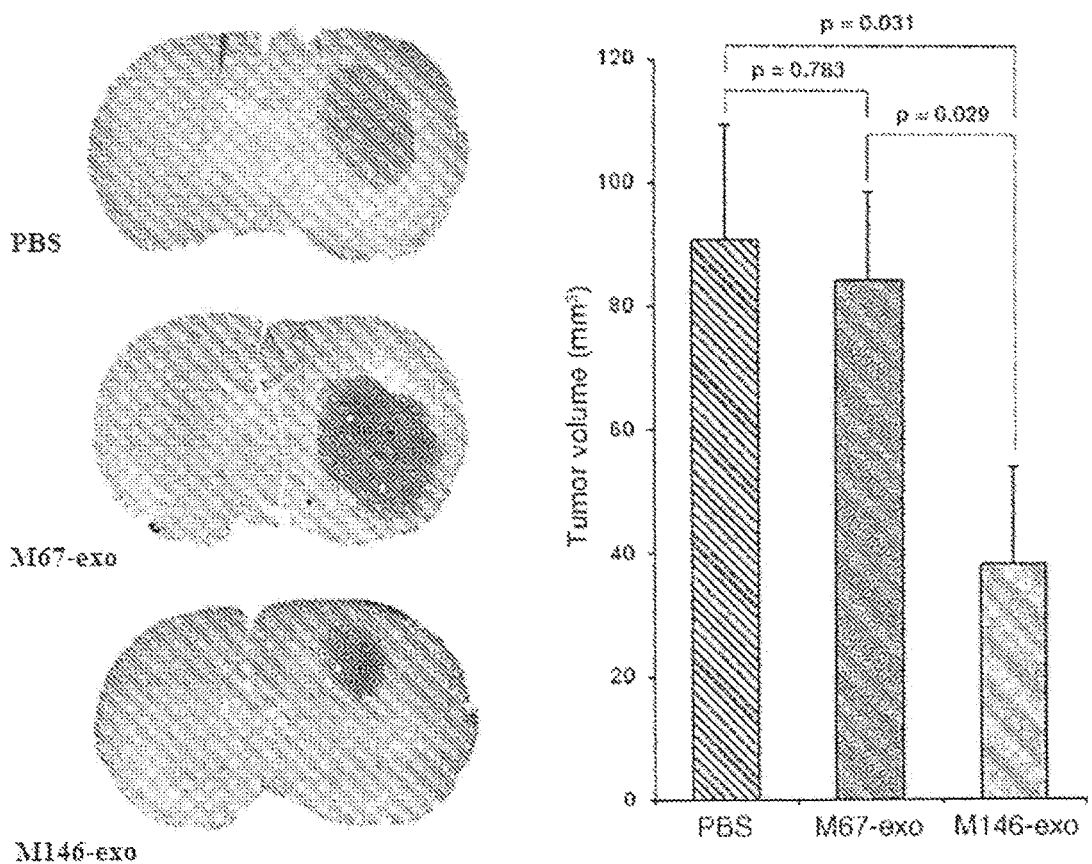
FIG. 5 is a data representation and images showing that exosomes from MSCs transfected with a miR-146b expression plasmid reduce tumor growth when administered to rats bearing 9 L gliosarcoma tumors.

To determine whether an anti-tumor miRNA packaged in MSC exosomes would reduce tumor growth in vivo, we treated rats bearing 9 L gliosarcoma brain tumors with these MSC exosomes package with miR-146b via intra-tumor administration. 24 Fischer rats were implanted with 9 L gliosarcoma. After 5 days, cel-miR-67-containing exosomes from cel-miR-67-transfected MSCs (control), or miR-146b-containing exosomes from miR-146b-transfected MSCs, or saline treatment were administered by intra-tumor injection (n=8 per treatment group). 10 days after tumor implantation, animals were sacrificed and tumor volume was calculated. As shown in FIG. 5, treatment with miR-146b-containing MSC exosomes significantly reduced tumor growth in rats bearing 9 L gliosarcoma tumors compared to cel-miR-67-containing MSC exosome control (cel-miR-67 does not have binding sites in rat mRNA). (FIG. 5 legend: PBS (vehicle only), M146-exo or cel-miR-67 exosomes ("M67-exo") was administered via intra-tumor injection 5 days after tumor implant. Animals were sacrificed at 10 days post-implant (n=8 per group). Bars are standard deviation.)

Example 4

Exosomes are generally 30-150 nm vesicles secreted by a wide range of mammalian cells that can contain miRNA. To determine whether MSC exosomes could be used as a vehicle for delivery of anti-tumor miRNAs, we transfected MSCs with a miR-146b expression plasmid, and harvested exosomes released by the MSCs. Intra-tumor injection of exosomes derived from miR-146-expressing MSCs significantly reduced glioma xenograft growth in a rat model of primary brain tumor.

Aberrant gene expression is a mechanism of miRNA dysfunction in cancer, including in GBMs, and miRNAs are differentially expressed in GBM relative to normal tissue. Human mir-146b is located on chromosome 10 within 10q24-26 (10q24.32, 104186259-104186331+), a region lost in a majority of these tumors. miR-146b reduces glioma cell motility and invasion, and EGFR mRNA is a binding-target for miR-146b silencing. EGFR gene amplification occurs in approximately 40% of all GBMs and increased EGFR correlates with glioma invasiveness and malignancy. We employed a 9 L xenograft model of primary brain tumor to determine whether miR-146b could function as an anti-glioma miRNA in vivo.

Materials and Methods:

Tumor Implantation.

Male Fischer rats (250-275 g) were used. A 2 mm diameter craniotomy was made on the right hemisphere anterior to the coronal suture. Using a Hamilton syringe, tumor cells were injected 3.5 mm deep, 3.0 mm to the right and 1.0 mm anterior of the bregma. Rats were implanted with $2.5 \times 10^5$ 9 L cells (5 lA PBS) over a 15-minute interval. The craniotomy was covered with Horsley's bone wax, and the incision was closed with 4-0 silk suture (Ethicon). Animals were weighed at tumor implantation, treatment, and prior to sacrifice. No statistical difference in weights was detected between treatment groups. Rats were sacrificed 10 days after implantation under anesthesia with i.p. administration of ketamine (100 mg/kg) and xylazine (10 mg/kg). Animals were perfused with 10% formalin following vascular washout with 0.9% saline. Brains were removed, fixed and cut into 2 mm thick blocks which were embedded in paraffin. Sections were stained with hematoxylin and eosin. To measure tumor volume, in each coronal section, the area of the tumor was measured using MCID software (InterFocus Imaging) by tracing the demarcation of the tumor, and the section volume was determined by multiplying the traced area by the section thickness.

Plasmids and MSC Transfection.

Cel-miR-67 and hsa-miR-146b expression plasmids (GenScript) were used. The plasmid used with respect to cel-miR-67 was the pRNA-CMV3.1/Puro plasmid, SEQ ID NO: 1; see also http://www.genscript.com/vector/SD1233-pRNA_CMV3_1_Puro.html, which is hereby incorporated by reference. The inserted cel-miR-67 sequence comprised SEQ ID NO: 2. The plasmid used with respect to has-miR-146b was the pEP-miR plasmid, SEQ ID NO: 3; see also http://www.cellbiolabs.com/sites/default/files/MIR-146B.pdf, which is hereby incorporated by reference. The inserted has-miR-146b sequence comprised SEQ ID NO: 4. MSC transfection was performed using electroporation. $2 \times 10^6$ MSCs were suspended in 150 µl of Ingenio Electroporation Solution (Minis) with 2 µg of plasmid DNA. Program A-33 was used for electroporation in an Amaxa Nucleofector Device. Transfected cells were resuspended in 10 ml complete culture medium, centrifuged, and then plated for exosome production.

Exosome Preparation and Harvest.

$2 \times 10^6$ MSCs were seeded in 10 ml Dulbecco's Modified Eagle Medium supplemented with 20% Fetal Bovine Serum. After 48 hours, exosomes were isolated from the MSC medium using ExoQuick-TC (System Biosciences, CA). Exosome pellets were resuspended in sterile PBS at a total protein concentration of 10 µl. Exosome suspensions were placed on ice and administered to animals within 6 hours following harvest. Exosomes visualized by electron microscopy were fixed in glutaraldehyde (5 µg/µl) for 30 minutes.

Exosome Treatment.

For treatment, 5 µl of the M67-exo or M146-exo suspension was injected in each animal via intra-tumor injection at 5 days after tumor implantation. Using a Hamilton syringe, exosome suspension or PBS vehicle was injected at the same coordinates as the tumor implant, over a 5-minute interval. Real-time PCR was used to determine relative cel-miR-67 expression and miR-146b expression in M67-exo and M146-exo used for treatment. MiR-146b was 7.3±1.7 fold higher in M146-exo compared to M67-exo. Cel-miR-67 was not detected in M146-exo, but was detected with a CT value of 33.2±2.3 in M67-exo.

Real-Time PCR.

To analyze miRNA expression, MSC cells, 9 L cells or MSC exosomes were lysed in Qiazol reagent and total RNA was isolated using the miRNeasy Mini kit (Qiagen). Reverse transcription was performed with the miRNA Reverse Transcription Kit (Applied Biosystems), and cDNA was amplified with TaqMan miRNA assays (Applied Biosystems), which are specific for mature miRNA sequences. 40 amplification cycles were performed. The 2-ΔΔCT method was used to determine relative miRNA expression. If a CT was not reached in 40 amplification cycles, the measured miRNA was considered to be undetected.

Western Blot.

$2 \times 10^5$ 9 L cells were seeded in a 6-well plate and cultured overnight. M67-exo or M146-exo (50 µg total protein) in 5 µl PBS was added to the culture medium. 24 hours later 9 L cells were lysed and Western blot was used to detect EGFR and β-actin (Santa Cruz Biotechnology). Protein concentration was quantified using a BCA protein assay kit (Pierce). SuperSignal West Pico Chemiluminescent Substrate (Pierce) and Kodak X-omat film (Kodak) exposure were used for visualization.

Statistical Analysis.

Data are shown as mean±s.e.m. P-values were calculated using one-way ANOVA or Student's t test. A p-value of 0.05 or less was considered statistically significant.

Figure 6A:
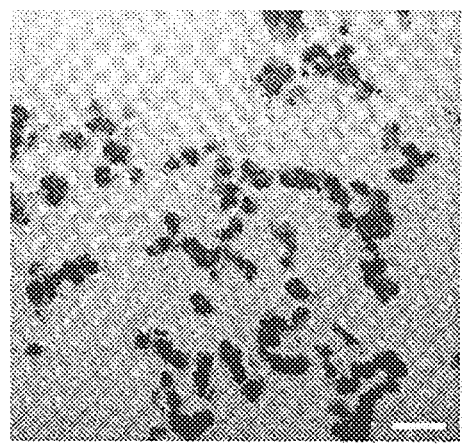
FIG. 6A is an image showing an electron micrograph of MSC exosomes isolated from MSC culture medium.
Figure 6B:
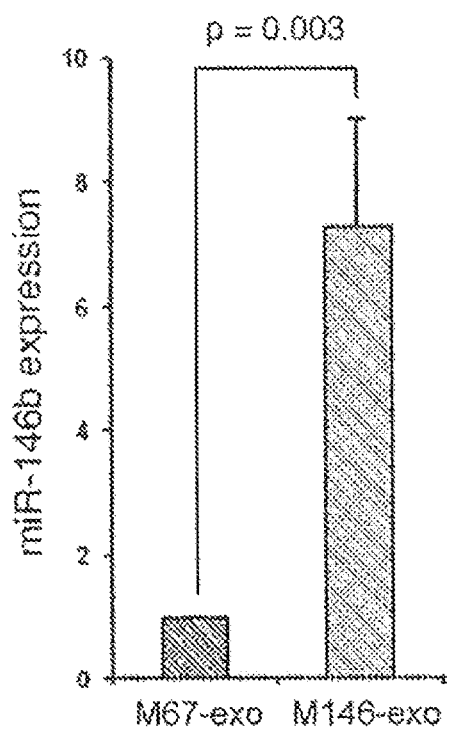
FIG. 6B is a graph showing real-time PCR detection of miR-146b expression in M67-exo and M146-exo.

Results:

To determine whether MSCs package miR-146b into secreted exosomes, we transfected MSCs from rats with a plasmid encoding for miR-146b, or for cel-miR-67, which has no known mRNA binding targets in rat. 48 hours after transfection, exosomes were isolated from the medium, and miR-146b and cel-miR-67 were measured in MSCs and extra-cellular exosomes. FIG. 6A shows exosomes from MSCs transfected with miR-146b or cel-miR-67 expression plasmids. (FIG. 6A: Electron micrograph of MSC exosomes isolated from MSC culture medium, Scalebar=500 nm) miR-146b was 7.1±3.7 fold higher in MSCs and 7.3±1.7 fold higher in MSC exosomes after miR-146b expression plasmid transfection, compared to miR-146 levels in cel-miR-67 plasmid transfected MSCs and their exosomes, respectively (FIG. 6B: real-time PCR detection of miR-146b expression in M67-exo and M146-exo (n=7). Data are mean±s.e.m.; comparison is two-tailed t-test.). Cel-miR-67 was not detected in miR-146b plasmid transfected MSCs or their exosomes (M146-exo), but was detected in cel-miR-67 plasmid transfected MSCs and their exosomes (M67-exo). These data demonstrate that plasmid-expressed miRNA is efficiently packaged into MSC exosomes by endogenous mechanisms.

Figure 6C:
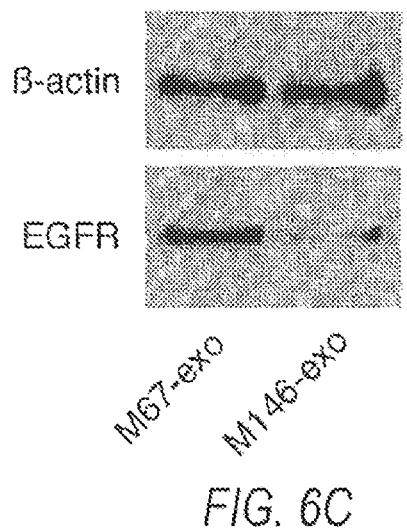
FIG. 6C is an image of a Western blot for R-actin and EGFR protein expression in 9 L cells treated with M67-exo and M146-exo.

To determine whether MSC exosomes carrying miR-146b deliver the miRNA into tumor cells, we exposed 9 L cells to M146-exo or M67-exo in vitro. After 24 hours, miR-146b detected in M146-exo-treated 9 L cells was 8.5±0.4 times higher compared to M67-exo-treated cells, whereas cel-miR-67 was detected in M67-exo-treated 9 L cells, but not detected M146-exo-treated cells. Thus, MSC exosomes can deliver plasmid-expressed miRNAs into tumor cells in vitro. To determine whether M146-exo could alter target protein expression in tumor cells, we exposed 9 L cells to M146-exo in vitro, and after 24 hours, EGFR protein levels were lower in M146-exo-treated 9 L cells compared to M67-exo-treated 9 L cells (FIG. 6C: Western blot for (β-actin and EGFR protein expression in 9 L cells treated with M67-exo and M146-exo.) These findings indicated to us that miR-146b, delivered via MSC exosomes, is functionally active in the acceptor tumor cells.

Figure 7A:
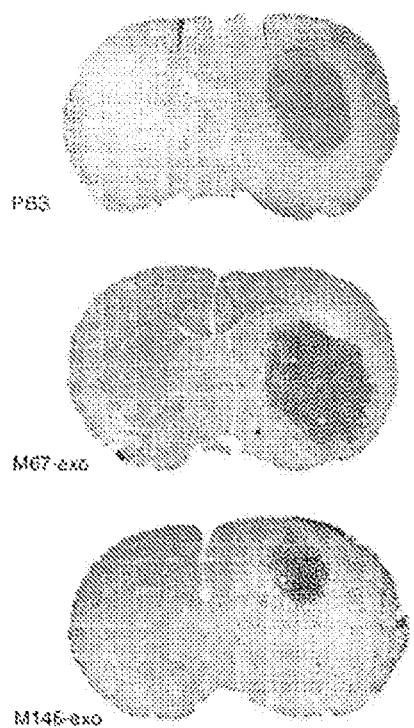
FIG. 7A is an image of representative H&E-stained coronal sections from sacrificed rats after tumor implantation.
Figure 7B:
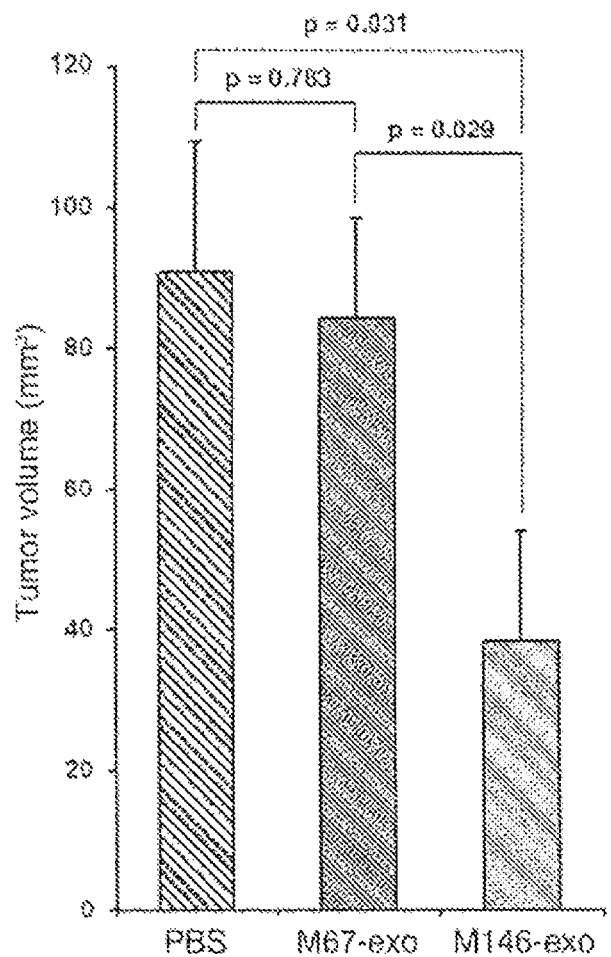
FIG. 7B is a graph of volumetric measurement of 9 L xenograft tumors.

Finally, to determine whether M146-exo had an anti-tumor effect in vivo, we administered M146-exo or M67-exo (50 μg total protein in 5 μl volume) to Fischer rats bearing 9 L gliosarcoma. We found that one intra-tumor injection of M146-exo 5 days after intracranial tumor xenograft implantation lead to a significant reduction in tumor volume at 10 days post-implant compared M67-exo or vehicle treated control (FIG. 7—A: Representative H&E-stained coronal sections from rats sacrificed 10 days after tumor implantation; B: Volumetric measurement of 9 L xenograft tumors 10 days after tumor implant, and 5 days after PBS, M67-exo, or M146-exo treatment (n=8 per group). ANOVA: p=0.042. Data are mean±s.e.m. Post hoc multiple comparisons are two-tailed t-tests.). These data indicated to us that M146-exo elicits an anti-tumor effect in the rat brain.

Here, one intra-tumor injection of 50 jug M146-exo significantly reduced glioma xenograft growth in rat brain. Our findings indicate to us that export of specific therapeutic miRNA into MSC exosomes represents a new treatment strategy for at least malignant glioma.

As discussed herein, some embodiments comprise a novel treatment whereby therapeutic miRNA that is produced in MSCs and loaded into extra-cellular exosomes by endogenous mechanisms, is used to treat tumor.

Interest is growing in using exosomes as biological delivery vehicles. Exosomes are taken up by acceptor cells, whereby cellular processes can be altered. There is some evidence that exosomes do not elicit acute immune rejection, and as they are nonviable, they do not risk tumor formation. Furthermore, exosomes can be manufactured at scale in culture, possibly using autologous cells, and exosome-producing cells could incorporate multiple therapeutic miRNAs, enabling personalized treatment. Our work indicates that miRNA packaged into MSC exosomes arc incorporated by tumor cells in culture. For in vivo treatment, we delivered exosomes directly by intra-tumor injection. There are indications that functional miRNAs are transferred between glioma cells, suggesting that therapeutic miRNAs may distribute throughout the tumor.

In some embodiments, without limitation or disclaimer, we employed MSCs as producer cells. However, other cell types may be employed as well to package miRNAs into exosomes. Once transfected, producer cells can create custom miRNA-bearing exosomes for an extended period of time. Thus, exosomes could be harvested at multiple time points and delivered to the patient over several days or weeks, or the producer cells themselves might be transplanted into the tissue to be treated to produce custom miRNA-bearing exosomes on site. Furthermore, the producer cells could be harvested from the patient's own bone marrow or other organs in order to limit any potential immune complications.

According to some embodiments useful in a clinical setting, therapeutic miRNAs could be packaged in exosomes, and these exosomes could be administered to the patient. Thus, depending upon the miRNAs that are packaged, a wide range of diseases could be treated with these custom exosomes.

According to some embodiments useful in a clinical setting, therapeutic miRNAs could be packaged in exosomes, and these exosomes could be frozen and stored for future administration to the patient. Thus, depending upon disease state, the patient's cells could be used to produce custom exosomes to be administered at a later time point.

In some embodiments, miRNAs are introduced into the MSCs (or other producer cells) to package the miRNAs in exosomes. However, the introduction of the miRNAs into the MSCs may alter the MSCs themselves, and importantly, the nature of the exosomes they produce. Thus, the resulting modification of the exosomes (and their other components) may have therapeutic effect in addition to the packaged miRNAs. MSCs (or other producer cells) can be transfected with miRNAs with the intent to modify the exosomes that are released.

Thus, without limitation and without disclaimer of subject matter, some embodiments comprise novel exosomes containing one or more selected miRNAs and/or producer cells containing same (collectively "modified exosome/producer cell administration") to prevent, control, or alleviate mammalian illness or injury through the selective application of such miRNAs. In accordance with some embodiments, without limitation, one may inhibit such illness or injury through modified exosome/producer cell administration for a finite interval of time, thereby limiting the development or course of such illness or injury.

In accordance with some embodiments, there is a high likelihood that the duration of therapy comprising modified exosome/producer cell administration would be relatively brief and with a high probability of success. Prophylactic modified exosome/producer cell administration of some embodiments may greatly reduce the incidence of damage associated with many forms of illness or injury.

Any appropriate routes of modified exosome/producer cell administration known to those of ordinary skill in the art may comprise some embodiments.

Modified exosomes/producer cells of some embodiments would be administered and dosed in accordance with good medical practice, taking into account the clinical condition of the individual patient, the site and method of administration, scheduling of administration, patient age, sex, body weight and other factors known to medical practitioners. The "pharmaceutically effective amount" for purposes herein is thus determined by such considerations as are known in the art. The amount must be effective to achieve improvement, including but not limited to, decreased damage or injury, or improvement or elimination of symptoms and other indicators as are selected as appropriate measures by those skilled in the art.

In accordance with some embodiments, modified exosomes/producer cells can be administered in various ways. They can be administered alone or as an active ingredient in combination with pharmaceutically acceptable carriers, diluents, adjuvants and vehicles. The modified exosomes/producer cells can be administered orally, subcutaneously or parenterally including intravenous, intraarterial, intramuscular, intraperitoneal, and intranasal administration as well as intrathecal and infusion techniques, or by local administration or direct inoculation to the site of disease or pathological condition. Implants of the modified exosomes/producer cells may also be useful. The patient being treated is a warm-blooded animal and, in particular, mammals including humans. The pharmaceutically acceptable carriers, diluents, adjuvants and vehicles as well as implant carriers generally refer to inert, non-toxic solid or liquid fillers, diluents or encapsulating material not reacting with the active components of some embodiments. In some embodiments, modified exosomes/producer cells may be altered by use of antibodies to cell surface proteins or ligands of known receptors to specifically target tissues of interest.

Since the use of modified exosomes/producer cells administration in accordance with some embodiments specifically targets the evolution, expression, or course of associated pathologies, it is expected that the timing and duration of treatment in humans may approximate those established for animal models in some cases. Similarly, the doses established for achieving desired effects using such compounds in animal models, or for other clinical applications, might be expected to be applicable in this context as well. It is noted that humans are treated generally longer than the experimental animals exemplified herein which treatment has a length proportional to the length of the disease process and drug effectiveness. The doses may be single doses or multiple doses over periods of time. The treatment generally has a length proportional to the length of the disease process and drug effectiveness and the patient species being treated.

When administering the modified exosomes/producer cells of some embodiments parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

When necessary, proper fluidity can be maintained, for example, by the use of a coating such as lecithin, by the maintenance of the required size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for such modified exosome/producer cell compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to some embodiments, however, any vehicle, diluent, or additive used would have to be compatible with the modified exosomes/producer cells.

Sterile injectable solutions can be prepared by incorporating modified exosomes/producer cells utilized in practicing the some embodiments in the required amount of the appropriate solvent with various other ingredients, as desired.

A pharmacological formulation of some embodiments may be administered to the patient in an injectable formulation containing any compatible carrier, such as various vehicle, adjuvants, additives, and diluents; or the inhibitor(s) utilized in some embodiments may be administered parenterally to the patient in the form of slow-release subcutaneous implants or targeted delivery systems such as monoclonal antibodies, vectored delivery, iontophoretic, polymer matrices, liposomes, and microspheres. Many other such implants, delivery systems, and modules are well known to those skilled in the art.

In some embodiments, without limitation, the modified exosomes/producer cells may be administered initially by intravenous injection to bring blood levels to a suitable level. The patient's levels are then maintained by an oral dosage form, although other forms of administration, dependent upon the patient's condition and as indicated above, can be used. The quantity to be administered and timing of administration may vary for the patient being treated.

Additionally, in some embodiments, without limitation, modified exosomes/producer cells may be administered in situ to bring internal levels to a suitable level. The patient's levels are then maintained as appropriate in accordance with good medical practice by appropriate forms of administration, dependent upon the patient's condition. The quantity to be administered and timing of administration may vary for the patient being treated.

Example 5

Anti-Inflammatory Effects Related to Administration of miR-146b Enriched Exosomes in Rat Brains.

Figure 8A:
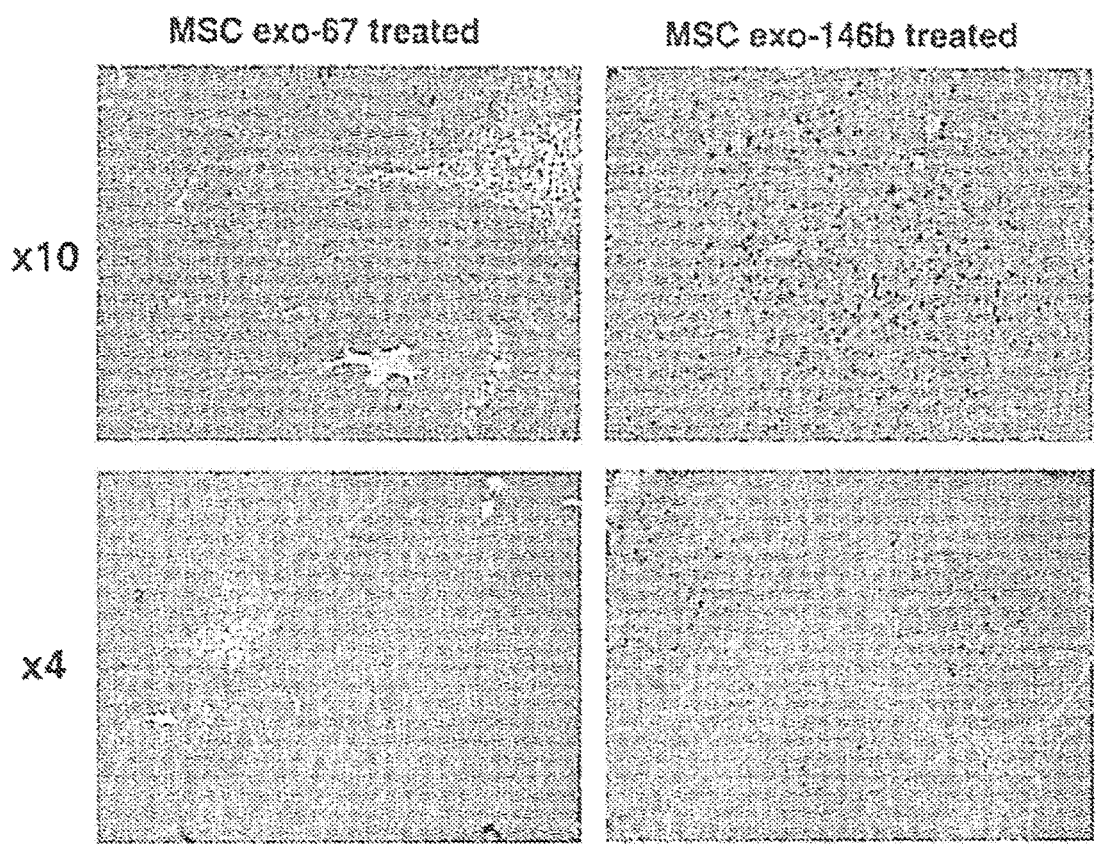
FIG. 8A depicts four representative photomicrographs of immune staining for arginase1 after miR-146b exosome treatment of a rat with MMI.
Figure 8B:
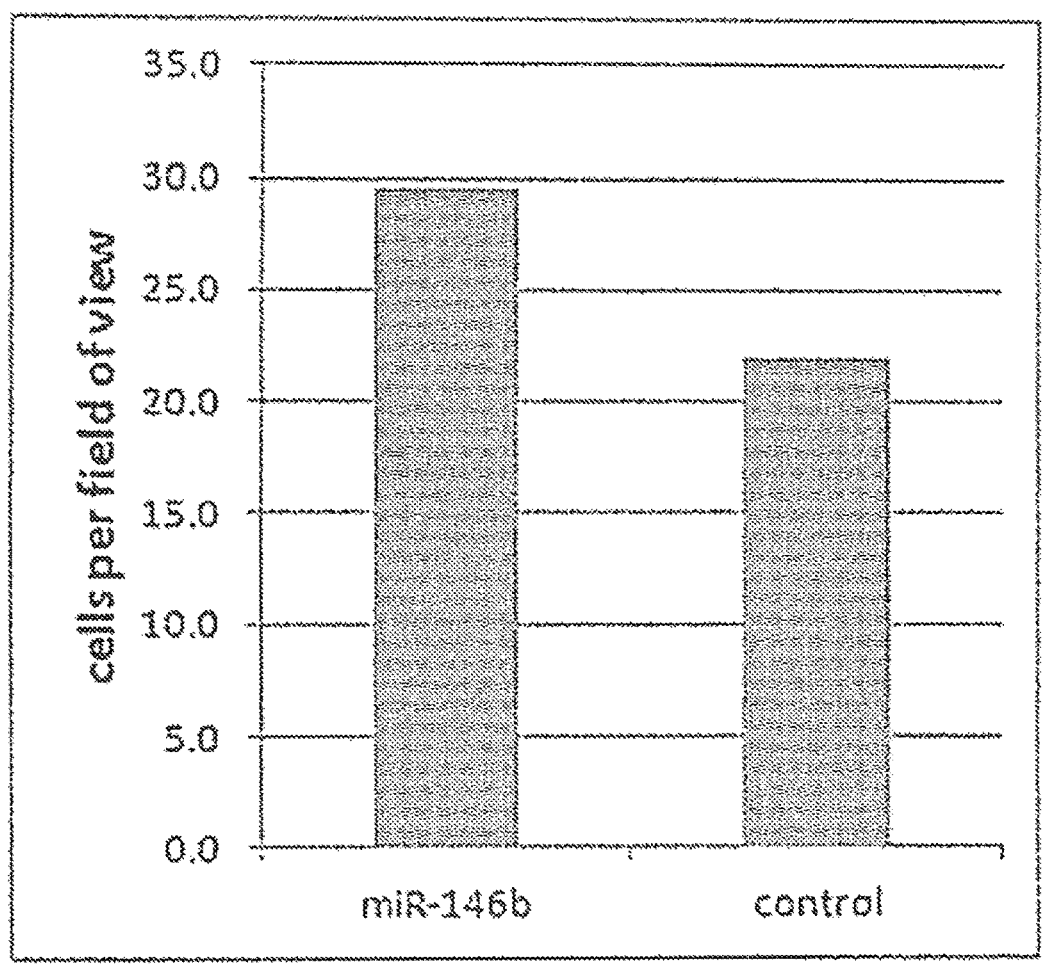
FIG. 8B depicts a bar graph quantifying the amount of arginase1 as depicted in FIG. 8A.

In the brains of rats, miR-146b enriched exosomes were administered stereotactically. After administration, induction of arginase1 (Arg1) in microglia (brain macrophages) was observed (See FIGS. 8A and 8B). In this experiment, we injected $10^4$ 9 L gliosarcoma cells into the brains of Fisher rats, and allowed them to grow for 7 days. At that time, a single bolus of miR-146b containing exosomes intratumorally into rats carrying a glioma xenograft. The xenografts were then allowed to grow for an additional 7 days, at which time the rats were sacrificed, and their brains fixed in 4% paraformaldehyde. We then sectioned the brains of these rats, and stained them for Arg1 with an anti-Arg1 monoclonal antibody and counted the total number of Arg1 reactive cells in and around the tumor. We found that Arg1 expression was significantly increased in the miR-146b exosome treatment cohort. Arg1 is a protein that is expressed in microglia, and has been shown to be associated with an anti-inflammatory phenotype. Significantly, we and others have shown microglia expressing an anti-inflammatory phenotype (i.e., those expressing Arg1) to be integral to functional recovery in many neurologic diseases, including stroke (1), Alzheimer's disease (2), traumatic brain injury (3), and multiple sclerosis (4).

Example 6

Anti-Inflammatory Properties of miR-146b

Figure 9:
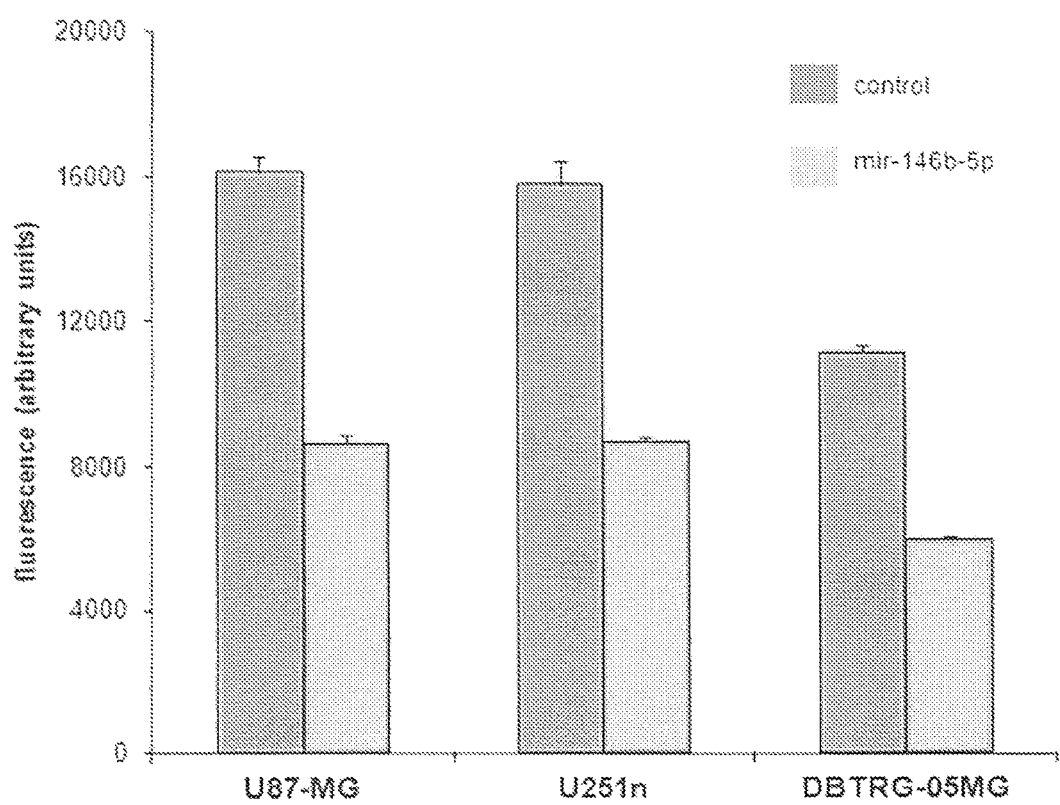
FIG. 9 depicts a bar graph quantifying the amount of α-secretase activity inhibition when exposed to exosomes containing miR-146b.

Several glioma cell lines were treated with miR-146b, their α-secretase activity was measured by a fluorescence assay. To measure alpha enzymatic activity, $2\times10^5$ cells were lysed and processed with an α-secretase Activity Kit (R&D Systems, Minneapolis, Minn., USA) per the manufacturer's instructions. Fluorescence was read using a Fusion Multiplate reader. Cells exposed to miR-146b exosomes were found to have lower α-secretase activity than control exosomes (FIG. 9). α-secretase activity measurement is a validated method for determining how much of a particular extracellular domain (known as an α domain) of some proteins is released into the extracellular space. Among the most important of the proteins that secrete an α domain is tumor necrosis factor-α (TNFα). TNFα is highly inflammatory, and inflammatory microglia are known to correlate with poor prognosis in cancer survival (5). Furthermore, we have also shown miR-146b to interrupt the IRAK/TRAF6/NF-κB pathway, which is also highly inflammatory (6). These data observed and correlations are believed to indicate that exosomes expressing miR-146b when made present in inflamed tissue, such as neurologic tissue of the brain, suppresses the inflammatory system in such a way that would likely make them efficacious at treating diseases that have a neuroinflammatory component. Neurological diseases that have a neuroinflammatory component are several, including those diseases that are also caused by or exacerbated by low oxygen conditions and demyelination. These diseases include but are not limited to stroke, brain injury, central pontine, dementia, multiple sclerosis (MS) (together with the similar diseases called idiopathic inflammatory demyelinating diseases), tumefactive multiple sclerosis, Solitary sclerosis, cognitive decline from aging, Alzheimer's disease, Parkinson's disease, epilepsy, migraine, neuropathy, for example, peripheral neuropathy, Vitamin B12 deficiency, myelinolysis, Tabes Dorsalis, transverse myelitis, Devic's neuromyelitis optica, fulminant or acute idiopathic inflammatory-demyelinating disease, Marburg variant of multiple sclerosis, Baló's concentric sclerosis, Schilder's disease, acute disseminated encephalomyelitis; transverse myelitis, optic neuritis, progressive multifocal leukoencephalopathy, acute hemorrhagic leukoencephalitis, acute disseminated encephalomyelitis, anti-myelin oligodendrocyte glycoprotein autoimmune encephalomyelitis, Leukodystrophy, adrenoleukodystrophy, adrenomyeloneuropathy, chronic inflammatory demyelinating polyradiculoneuropathy (CIDP), Guillain-Barre syndrome, chronic inflammatory demyelinating polyneuropathy, and anti-MAG peripheral neuropathy.

Example 7

Cell-Based Therapy for Vascular Dementia

Figure 10:
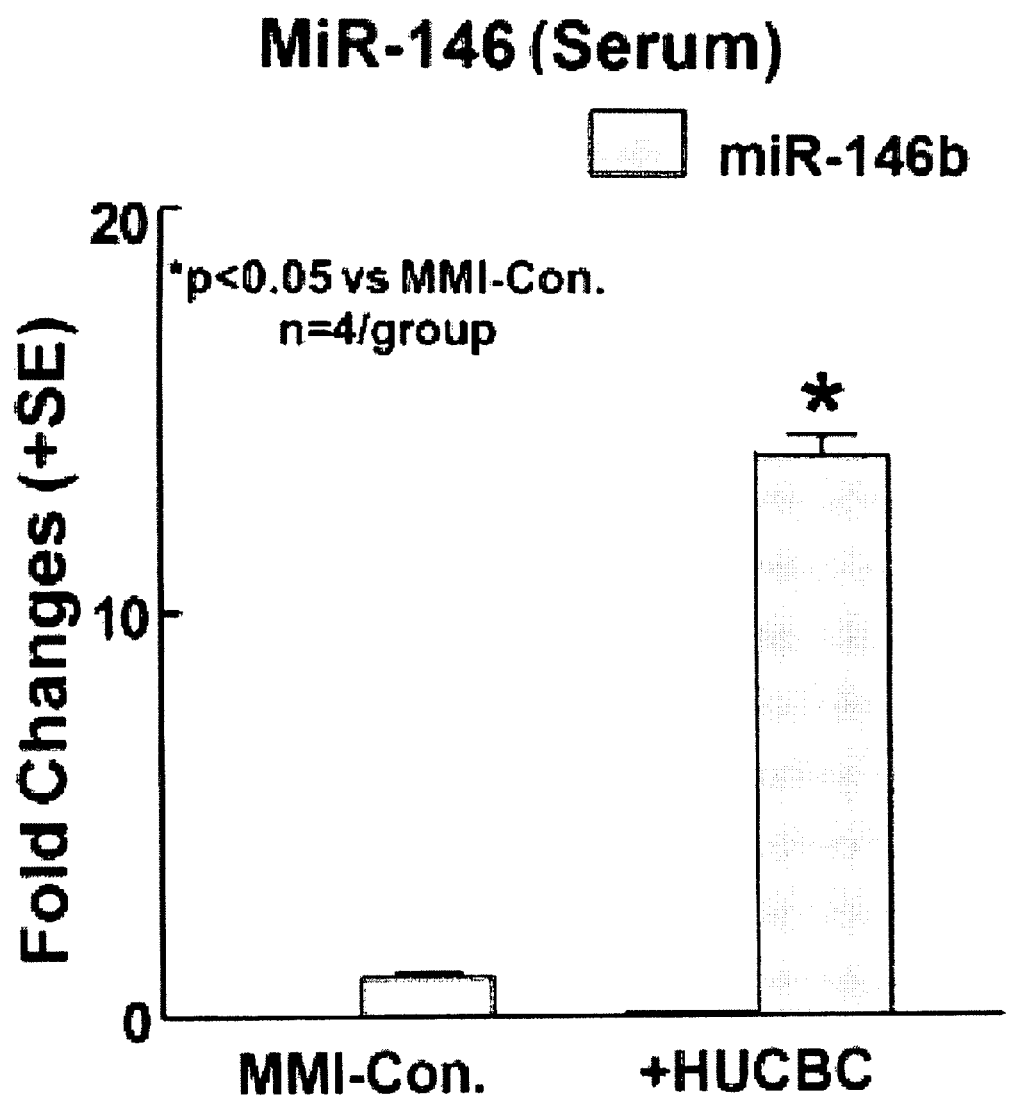
FIG. 10 depicts a bar graph quantifying the degree of functional recovery of animals when dosed with MSC exosomes, indicating a higher expression level of miR-146b in animals that have better recovery compared to MMI controls.

In a first set of experiments, animals subjected to our multiple micro-infarct (MMI) model, a model of vascular dementia, are injected with exosomes from mesenchymal stem cells (MSCs), and observed post implantation for cognitive recovery and behavior. Rats were observed to recover faster, and more completely than control MMI animals, based on motor and cognitive testing. In this model, 500 cholesterol crystals of diameter 70-100 μm in a 300 μL bolus of phosphate buffered saline are injected into the internal carotid artery of anesthetized rats. The crystals created many small infarctions when they reach a branch point in the cerebral vasculature through which they are too large to pass. This model created functional and cognitive deficits that mimic vascular dementia, since none of the infarcts are severe enough to create a stroke-like condition. We subjected 12 rats to this model, and randomized them into control, and exosome treated. In this experiment, the exosomes were derived from human umbilical cord blood cells. During the recovery phase, we collected blood from each animal to determine what factors correlate with enhanced functional recovery. We isolated exosomes from the blood and amplified the RNA contents by real time RT-PCR. Our data show that exosome-induced enhancement of recovery is commensurate with increased circulating miR-146b in the blood of exosome treated animals (FIG. 10). We have observed fewer inflammatory cells in the infracted zone after exosome treatment, and it is likely that miR-146b is a major component of the animals' enhanced recovery. Together, these data indicate that our invention of miR-146b containing exosomes for treatment of injuries and disease is a generalized mechanism and not specific to glioma.

Example 8

Treatment of Stroke with Exosomes Enriched with Micro-RNAs

We have investigated the mechanistic role of specific miRNAs in recovery from several brain diseases, and then packaged such miRNAs individually or in combination into MSC exosomes, and treated animals subjected to stroke.

Figure 11A:
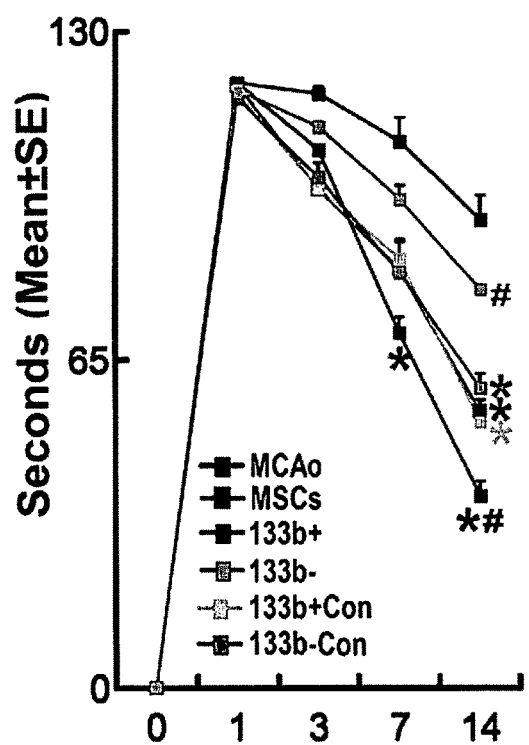
FIG. 11A depicts a line graph illustrating latency for a rat to remove an adhesive sticker from its paw after treatment with exosomes containing miR-133b.
Figure 11B:
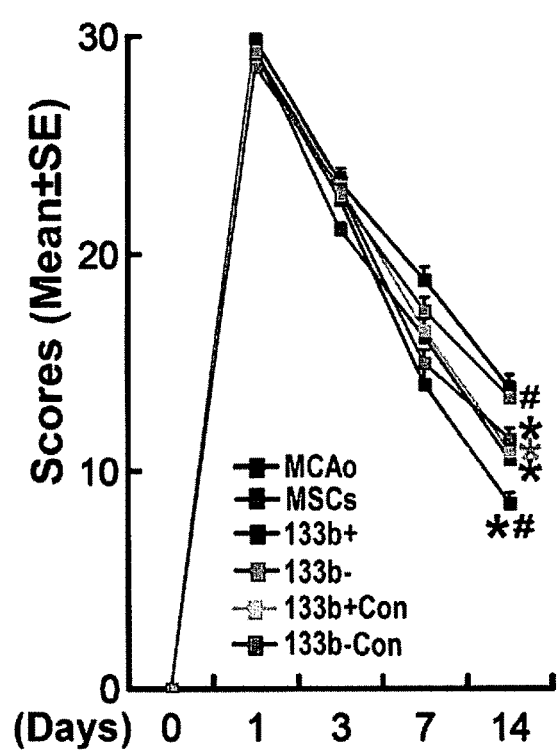
FIG. 11B depicts a line graph illustrating severity of stroke score after treatment with exosomes containing miR-133b.

Firstly, we treated rats that were subjected to experimental stroke with MSC exosomes that contained miR-133b, a miRNA that we and others showed to promote growth of injured neurons (7, 8). Animals were subjected to transient middle cerebral artery occlusion (MCAo). In this model, the external carotid artery is ligated, and a nylon filament with a blunted and is advanced from the internal carotid artery to the origin of the MCA. The blunted end of the filament inhibits the blood flow through the MCA, and is left in place for two hours, when it is removed so that blood can reperfuse the infracted region. The animals were randomized into several groups: control, naïve exosomes, exosomes overexpressed with miR-133b, exosomes from cells lacking miR-133b, and control exosomes from each experimental condition. Animals were given a single bolus of approximately $10^{11}$ exosomes at 24 hours after MCAo, and their functional recovery was tested periodically for two weeks by adhesive removal test and modified neurologic severity score (mNSS). Adhesive removal test involves measuring the time it takes for a rat to remove a sticker from its paw, and mNSS measure a battery of behavioral parameters and assigns "points" for each deficit, so that a higher score indicates poorer functional capacity. We found that after treatment on both of these measures, the animals treated with naïve exosomes performed better than no treatment controls, but animals treated with miR-133b enriched exosomes recovered faster and more completely than naïve exosome treated animals. The animals were sacrificed at the conclusion of functional testing, and their brains preserved in 4% paraformaldehyde. The brains were sectioned and stained for several markers of axons and myelin. Histology showed that miR-133b exosome treated animals had better repair of neuronal tracts than control (See FIGS. 11A and 11B).

We have investigated the mechanistic role of another set of miRNAs that are co-expressed, the miR-17~92 cluster, which comprises at least 6 individual miRNA. We previously found that theses miRNAs specifically speed the growth of the axons of new neurons, as well as speed the regrowth of injured axons (9). We applied these findings to our method of overexpressing miRNAs in MSC exosomes, and we confirmed the presence of constituent members of the cluster by real-time RT-PCR. We found that these exosomes were able to promote axonal growth more efficiently than exosomes alone, and that miR-17~92 overexpression activated the PTEN/mTOR pathway in the treated cells (10), which is significant since this pathway can promote growth generally, and is not brain specific. Our data also indicate that these exosomes promote functional recovery after experimental stroke. Therefore, our system of increasing expression of specific miRNAs is functional in specific pathways that are predictable and generalizable, and can therefore theoretically be applied in any disease in which one is able to show that a given miRNA has functional repercussions, for example in neuroinflammatory diseases, ischemic diseases and demyelination diseases.

Based on these data, it is believed that the data supports (a) treatment of neuroinflammatory diseases, ischemic diseases and demyelination diseases with miR-146b-containing exosomes, and the (b) we can generalize our findings regarding engineering of MSC exosomes to any arbitrary miRNA.

REFERENCES

1. Nair S M, Rahman R M, Clarkson A N, Sutherland B A, Taurin S, Sammut I A, Appleton I. Melatonin treatment following stroke induction modulates L-arginine metabolism. J Pineal Res. 2011; 51(3):313-23. doi: 10.1111/j.1600-079X.2011.00891.x. PubMed PMID: 21605165.
2. Cherry J D, Olschowka J A, O'Banion M K. Arginase 1+ microglia reduce Abeta plaque deposition during IL-1beta-dependent neuroinflammation. J Neuroinflammation. 2015; 12:203. doi: 10.1186/s12974-015-0411-8. PubMed PMID: 26538310; PMCID: PMC4634600.
3. Cao T, Thomas T C, Ziebell J M, Pauly J R, Lifshitz J. Morphological and genetic activation of microglia after diffuse traumatic brain injury in the rat. Neuroscience. 2012; 225:65-75. doi: 10.1016/j.neuroscience.2012.08.058. PubMed PMID: 22960311; PMCID: PMC3489473.
4. Stojanovic I, Vojinovic S, Ljubisavljevic S, Pavlovic R, Basic J, Pavlovic D, Ilic A, Cvetkovic T, Stukalov M. INF-beta1b therapy modulates L-arginine and nitric oxide metabolism in patients with relapse remittent multiple sclerosis. Journal of the neurological sciences. 2012; 323(1-2):187-92. doi: 10.1016/j.jns.2012.09.014. PubMed PMID: 23026532.
5. Dijksterhuis J P, Arthofer E, Marinescu V D, Nelander S, Uhlen M, Ponten F, Mulder J, Schulte G. High levels of WNT-5A in human glioma correlate with increased presence of tumor-associated microglia/monocytes. Exp Cell Res. 2015; 339(2):280-8. doi: 10.1016/j.yexcr.2015.10.022. PubMed PMID: 26511503.
6. Katakowski M, Buller B, Zheng X, Lu Y, Rogers T, Osobamiro O, Shu W, Jiang F, Chopp M. Exosomes from marrow stromal cells expressing miR-146b inhibit glioma growth. Cancer letters. 2013; 335(1):201-4. doi: 10.1016/j.canlet.2013.02.019. PubMed PMID: 23419525; PMCID: 3665755.
7. Yu Y M, Gibbs K M, Davila J, Campbell N, Sung S, Todorova T I, Otsuka S, Sabaawy H E, Hart R P, Schachner M. MicroRNA miR-133b is essential for functional recovery after spinal cord injury in adult zebrafish. The European journal of neuroscience. 2011; 33(9):1587-97. doi: 10.1111/j.1460-9568.2011.07643.x. PubMed PMID: 21447094; PMCID: PMC3100659.
8. Xin H, Li Y, Buller B, Katakowski M, Zhang Y, Wang X, Shang X, Zhang Z G, Chopp M. Exosome-mediated transfer of miR-133b from multipotent mesenchymal stromal cells to neural cells contributes to neurite outgrowth. Stem cells. 2012; 30(7):1556-64. doi: 10.1002/stem.1129. PubMed PMID: 22605481; PMCID: PMC3495063.
9. Zhang Y, Ueno Y, Liu X S, Buller B, Wang X, Chopp M, Zhang Z G. The MicroRNA-17-92 cluster enhances axonal outgrowth in embryonic cortical neurons. The Journal of neuroscience: the official journal of the Society for Neuroscience. 2013; 33(16):6885-94. doi: 10.1523/JNEUROSCI.5180-12.2013. PubMed PMID: 23595747; PMCID: PMC3657758.
10. Zhang Y, Chopp M, Liu X S, Katakowski M, Wang X, Tian X, Wu D, Zhang Z G. Exosomes Derived from Mesenchymal Stromal Cells Promote Axonal Growth of Cortical Neurons. Mol Neurobiol. 2016. doi: 10.1007/s12035-016-9851-0. PubMed PMID: 26993303; PMCID: PMC5028236.

While the some embodiments have been particularly shown and described with reference to the foregoing preferred and alternative embodiments, it should be understood by those skilled in the art that various alternatives to the embodiments described herein may be employed in practicing the invention without departing from the spirit and scope of the invention as defined in the following claims. It is intended that the following claims define the scope of the invention and that the method and apparatus within the scope of these claims and their equivalents be covered thereby. This description of the some embodiments should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

SEQUENCES

```
SEQ ID NO: 1 -
TAGTTATTAATAGTAATCAATTACGGGGTCATTAGTTCATAGCCCATATA
TGGAGTTCCGCGTTACATAACTTACGGTAAATGGCCCGCCTGGCTGACCG
CCCAACGACCCCCGCCCATTGACGTCAATAATGACGTATGTTCCCATAGT
AACGCCAATAGGGACTTTCCATTGACGTCAATGGGTGGAGTATTTACGGT
```

| SEQUENCES |
|---|
| AAACTGCCCACTTGGCAGTACATCAAGTGTATCATATGCCAAGTACGCCC |
| CCTATTGACGTCAATGACGGTAAATGGCCCGCCTGGCATTATGCCCAGTA |
| CATGACCTTATGGGACTTTCCTACTTGGCAGTACATCTACGTATTAGTCA |
| TCGCTATTACCATGGTGATGCGGTTTTGGCAGTACATCAATGGGCGTGGA |
| TAGCGGTTTGACTCACGGGGATTTCCAAGTCTCCACCCCATTGACGTCAA |
| TGGGAGTTTGTTTTGGCACCAAAATCAACGGGACTTTCCAAAATGTCGTA |
| ACAACTCCGCCCCATTGACGCAAATGGGCGGTAGGCGTGTACGGTGGGAG |
| GTCTATATAAGCAGAGCTGGTTTAGTGAACCGTGGATCCCGTCGCTTACC |
| GATTCAGAATGGTTGATATCCGCCATTCTGAATCGGTAAGCGACGAAGCT |
| TAATAAAGGATCTTTTATTTTCATTGGATCTGTGTGTTGGTTTTTTGTGT |
| GCGGCCGCCCTCGACTGTGCCTTCTAGAAGACAATAGCAGGCATGCTGGG |
| GATGCGGTGGGCTCTATGGCTTCTGAGGCGGAAGAACCAGCTGGGGCTC |
| TAGGGGGTATCCCCACGCGCCCTGTAGCGGCGCATTAAGCGCGGCGGGTG |
| TGGTGGTTACGCGCAGCGTGACCGCTACACTTGCCAGCGCCCTAGCGCCC |
| GCTCCTTTCGCTTTCTTCCCTTCCTTTCTCGCCACGTTCGCCGGCTTTCC |
| CCGTCAAGCTCTAAATCGGGGCTCCCTTTAGGGTTCCGATTTAGTGCTT |
| TACGGCACCTCGACCCCAAAAAACTTGATTAGGGTGATGGTTCACGTAGT |
| GGGCCATCGCCCTGATAGACGGTTTTTCGCCCTTTGACGTTGGAGTCCAC |
| GTTCTTTAATAGTGGACTCTTGTTCCAAACTGGAACAACACTCAACCCTA |
| TCTCGGTCTATTCTTTTGATTTATAAGGGATTTTGCCGATTTCGGCCTAT |
| TGGTTAAAAAATGAGCTGATTTAACAAAAATTTAACGCGAATTAATTCTG |
| TGGAATGTGTGTCAGTTAGGGTGTGGAAAGTCCCCAGGCTCCCCAGCAGG |
| CAGAAGTATGCAAAGCATGCATCTCAATTAGTCAGCAACCAGGTGTGGAA |
| AGTCCCAGGCTCCCCAGCAGGCAGAAGTATGCAAAGCATGCATCTCAAT |
| TAGTCAGCAACCATAGTCCCGCCCCTAACTCCGCCCATCCCGCCCCTAAC |
| TCCGCCCAGTTCCGCCCATTCTCCGCCCCATGGCTGACTAATTTTTTTTA |
| TTTATGCAGAGGCCGAGGCCGCCTCTGCCTCTGAGCTATTCCAGAAGTAG |
| TGAGGAGGCTTTTTGGAGGCCTAGGCTTTTGCAAAAAGCTCCCGGGATG |
| ACCGAGTACAAGCCCACGGTGCGCCTCGCCACCCGCGACGACGTCCCCGCG |
| GCCGTACGCACCCTCGCCGCCGCGTTCGCCGACTACCCCGCCACGCGCC |
| ACACCGTCGACCCGGACCGCCACATCGAGCGGGTCACCGAGCTGCAAGAA |
| CTCTTCCTCACGCGCGTCGGGCTCGACATCGGCAAGGTGTGGGTCGCGGA |
| CGACGGCGCCGCGGTGGCGGTCTGGACCACGCCGGAGAGCGTCGAAGCGG |
| GGGCGGTGTTCGCCGAGATCGGCCCGCGCATGGCCGAGTTGAGCGGTTCC |
| CGGCTGGCCGCGCAGCAACAGATGGAAGGCCTCCTGGCGCCGCACCGGCC |
| CAAGGGAGCCCGCGTGGTTCCTGGCCACCGTCGGCGTCTCGCCCGACCACC |
| AGGGCAAGGGTCTGGGCAGCGCGTCGTGCTCCCCGGAGTGGAAGCCGCC |
| GAGCGCGCCGGGGTGCCCGCCTTCCTGGAGACCTCCGCGCCCCGCAACCT |
| CCCCTTCTACGAGCGGCTCGGCTTCACCGTCACCGCCGACGTCGAGGTGC |
| CCGAAGGACCGCGCACCTGGTGCATGACCCGCAAGCCCGGTGCCTGATTC |
| GAATGACCGACCAAGCGACGCCCAACCTGCCATCACGAGATTTCGATTCC |
| ACCGCCGCCTTCTATGAAAGGTTGGGCTTCGGAATCGTTTTCCGGGACGC |
| CGGCTGGATGATCCTCCAGCGCGGGGATCTCATGCTGGAGTTCTTCGCCC |
| ACCCCAACTTGTTTATTGCAGCTTATAATGGTTACAAATAAAGCAATAGC |
| ATCACAAATTTCACAAATAAAGCATTTTTTCACTGCATTCTAGTTGTGG |
| TTTGTCCAAACTCATCAATGTATCTTATCATGTCTGTATACCGTCGACCT |
| CTAGCTAGAGCTTGGCGTAATCATGGTCATAGCTGTTTCCTGTGTGAAAT |
| TGTTATCCGCTCACAATTCCACACAACATACGAGCCGGAAGCATAAAGTG |
| TAAAGCCTGGGGTGCCTAATGAGTGAGCTAACTCACATTAATTGCGTTGC |
| GCTCACTGCCCGCTTTCCAGTCGGGAAACCTGTCGTGCCAGCTGCATTAA |
| TGAATCGGCCAACGCGCGGGGAGAGGCGGTTTGCGTATTGGGCGCTCTTC |
| CGCTTCCTCGCTCACTGACTCGCTGCGCTCGGTCGTTCGGCTGCGGCGAG |
| CGGTATCAGCTCACTCAAAGGCGGTAATACGGTTATCCACAGAATCAGGG |
| GATAACGCAGGAAAGAACATGTGAGCAAAAGGCCAGCAAAAGGCCAGGAA |
| CCGTAAAAAGGCCGCGTTGCTGGCGTTTTTCCATAGGCTCCGCCCCCCTG |
| ACGAGCATCACAAAAATCGACGCTCAAGTCAGAGGTGGCGAAACCCGACA |
| GGACTATAAAGATACCAGGCGTTTCCCCCTGGAAGCTCCCTCGTGCGCTC |
| TCCTGTTCCGACCCTGCCGCTTACCGGATACCTGTCCGCCTTTCTCCCTT |
| CGGGAAGCGTGGCGCTTTCTCATAGCTCACGCTGTAGGTATCTCAGTTCG |
| GTGTAGGTCGTTCGCTCCAAGCTGGGCTGTGTGCACGAACCCCCCGTTCA |
| GCCCGACCGCTGCGCCTTATCCGGTAACTATCGTCTTGAGTCCAACCCGG |
| TAAGACACGACTTATCGCCACTGGCAGCAGCCACTGGTAACAGGATTAGC |
| AGAGCGAGGTATGTAGGCGGTGCTACAGAGTTCTTGAAGTGGTGGCCTAA |
| CTACGGCTACACTAGAAGAACAGTATTTGGTATCTGCGCTCTGCTGAAGC |
| CAGTTACCTTCGGAAAAGAGTTGGTAGCTCTTGATCCGGCAAACAAACC |
| ACCGCTGGTAGCGGTTTTTTTGTTTGCAAGCAGCAGATTACGCGCAGAAA |
| AAAAGGATCTCAAGAAGATCCTTTGATCTTTTCTACGGGGTCTGACGCTC |
| AGTGGAACGAAAACTCACGTTAAGGGATTTTGGTCATGAGATTATCAAA |
| AGGATCTTCACCTAGATCCTTTTAAATTAAAAATGAAGTTTTAAATCAAT |
| CTAAAGTATATATGAGTAAACTTGGTCTGACAGTTACCAATGCTTAATCA |
| GTGAGGCACCTATCTCAGCGATCTGTCTATTTCGTTCATCCATAGTTGCC |
| TGACTCCCCGTCGTGTAGATAACTACGATACGGGAGGGCTTACCATCTGG |
| CCCCAGTGCTGCAATGATACCGCGAGACCCACGCTCACCGGCTCCAGATT |
| TATCAGCAATAAACCAGCCAGCCGGAAGGGCCGAGCGCAGAAGTGGTCCT |
| GCAACTTTATCCGCCTCCATCCAGTCTATTAATTGTTGCCGGGAAGCTAG |
| AGTAAGTAGTTCGCCAGTTAATAGTTTGCGCAACGTTGTTGCCATTGCTA |
| CAGGCATCGTGGTGTCACGCTCGTCGTTTGGTATGGCTTCATTCAGCTCC |
| GGTTCCCAACGATCAAGGCGAGTTACATGATCCCCCATGTTGTGCAAAAA |
| AGCGGTTAGCTCCTTCGGTCCTCCGATCGTTGTCAGAAGTAAGTTGGCCG |
| CAGTGTTATCACTCATGGTTATGGCAGCACTGCATAATTCTCTTACTGTC |
| ATGCCATCCGTAAGATGCTTTTCTGTGACTGGTGAGTACTCAACCAAGTC |
| ATTCTGAGAATAGTGTATGCGGCGACCGAGTTGCTCTTGCCCGGCGTCAA |
| TACGGGATAATACCGCGCCACATAGCAGAACTTTAAAAGTGCTCATCATT |
| GGAAAACGTTCTTCGGGGCGAAAACTCTCAAGGATCTTACCGCTGTTGAG |
| ATCCAGTTCGATGTAACCCACTCGTGCACCCAACTGATCTTCAGCATCTT |
| TTACTTTCACCAGCGTTTCTGGGTGAGCAAAACAGGAAGGCAAATGCC |
| GCAAAAAAGGGAATAAGGGCGACACGGAAATGTTGAATACTCATACTCTT |
| CCTTTTTCAATATTATTGAAGCATTTATCAGGGTTATTGTCTCATGAGCG |
| GATACATATTTGAATGTATTTAGAAAAATAAACAAATAGGGGTTCCGCGC |
| ACATTTCCCCGAAAAGTGCCACCTGACGTCGACGGATCGGGAGATCTCCC |
| GATCCCCTATGGTGCACTCTCAGTACAATCTGCTCTGATGCCGCATAGTT |
| AAGCCAGTATCTGCTCCCTGCTTGTGTGTTGGAGGTCGCTGAGTAGTGCG |
| CGAGCAAAATTTAAGCTACAACAAGGCAAGGCTTGACCGACAATTGCATG |
| AAGAATCTGCTTAGGGTTAGGCGTTTTGCGCTGCGTTCGCGATGTACGGGC |
| CAGATATACGCGTTGACATTGATTATTGAC |

SEQ ID NO: 2 -
GGATCCTCACAACCTCCTAGAAAGAGTAGATTGATATCCGTCTACTCTTT
CTAGGAGGTTGTGACGAAGCTT

SEQ ID NO: 3 -
cccaactttt aaaagaaaag gggggattgg ggggtacagt
gcaggggaaa gaatagtaga cataatagca acagacatac
aaactaaaga attacaaaaa caaattacaa aattcaaaat
tttatcgatg cctccccgtc accaccccc ccaacccgcc
ccgaccggag ctgagagtaa ttcatacaaa aggactcgcc
cctgccttgg ggaatcccag ggaccgtcgt taaactccca
ctaacgtaga acccagagat cgctgcgttc ccgcccctc
accccgcccgc tctcgtcatc actgaggtgg agaagagcat
gcgtgaggct ccggtgcccg tcagtgggca gagcgcacat
cgcccacagt ccccgagaag ttgggggag gggtcggcaa
ttgaaccggt gcctagagaa ggtggcgcgg ggtaaactgg
gaaagtgatg tcgtgtactg gctccgcctt tttcccgagg
gtgggggaga accgtatata agtgcagtag tcgccgtgaa
cgttcttttt cgcaacgggt ttgccgccag aacacaggta
agtgccgtgt gtggttcccg cgggcctggc ctctttacgg
gttatggccc ttgcgtgcct tgaattactt ccacgcccct
ggctgcagta cgtgattctt gatcccgagc ttcggggttgg
aagtgggtgg gagagttcga ggccttcgcg ttaaggagcc
ccttcgcctc gtgcttgagt tgaggcctgg cctgggcgct
ggggccgccg cgtgcgaatc tggtggcacc ttcgcgcctg
tctcgctgct ttcgataagt ctctagccat ttaaaatttt
tgatgatatc ctgcgacgct ttttttctgt caagatagtc
ttgtaaatgc gggccaagat ctgcacactg gtatttcggt
ttttggggcc gcgggcggcg acggggcccg tgcgtcccag
cgcacatgtt ccgcaggagc gggcctgcga gcgcggccac
cgagaatcgg acgggggtag tctcaagctg gccggcctgc
tctggtgcct ggcctcgcgc cgccgtgtat cgccccgccc
tgggcggcaa ggctggcccg gtcggcacca gttgcgtgag
cggaaagatg gccgcttccc ggcctgctg caggggagctc
aaaatggagg acgcgcgct cgggagacgg ggcgggtgag
tcacccacac aaaggaaaag ggccttttccg tcctcagccg
tcgcttcatg tgactccacg gagtaccggg cgccgtccag
gcaccctgat tagttcctga ggatccnnnn nnnnnnnnnn
nnnnnnnnnn nnnnnnnnnn nnnnnnnnnn nnnnnnnnnn
nnnnnnnnnn nnnnnnnnnn nnnnnnnnnn nnnnnnnnnn
nnnnnngcta gctcgagctt ttggagtacg tcgtctttag
gttgggggga ggggttttat gcgatggagt ttccccacac
tgagtgggtg gagactgaag ttaggccagc ttggcacttg
atgtaattct ccttggaatt tgcccttttt gagtttggat
cttggttcat tctcaagcct cagacagtgt ttcaaagttt
ttttcttcca tttcaggtgt cgtgaaaact acccctctag
agtcgagcta ccggtcgcca ccatggtgag caagggcgag
gaggataaca tggccatcat caaggagttc atgcgcttca
aggtgcacat ggagggctcc gtgaacggcc acgagttcga
gatcgagggc gagggcgagg gccgccccta cgagggcacc
cagaccgcca agctgaaggt gaccaagggt ggccccctgc
ccttcgcctg ggacatcctg tcccctcagt tcatgtacgg
ctccaaggcc tacgtgaagc accccgccga catccccgac
tacttgaagc tgtccttccc cgagggcttc aagtgggagc
gcgtgatgaa cttcgaggac ggcggcgtgg tgaccgtgac
ccaggactcc tccctgcagg acggcgagtt catctacaag
gtgaagctgc gcggcaccaa cttcccctcc gacggccccg
taatgcagaa gaagaccatg ggctgggagg cctcctccga

SEQUENCES

```
gcggatgtac cccgaggacg gcgccctgaa gggcgagatc
aagcagaggc tgaagctgaa ggacggcggc cactacgacg
ctgaggtcaa gaccacctac aaggccaaga agcccgtgca
gctgcccggc gcctacaacg tcaacatcaa gttggacatc
acctccacaa acgaggacta caccatcgtg aacagtacg
aacgcgccga gggccgccac tccaccggcg gcatggacga
gctgtacaag gacccaccgg tcgccaccat gaccgagtac
aagcccacgg tgcgcctcgc cacccgcgac gacgtcccca
gggccgtacg caccctcgcc gccgcgttcg ccgactaccc
cgccacgcgc cacaccgtcg atccggaccg ccacatcgag
cgggtcaccg agctgcaaga actcttcctc acgcgcgtcg
ggctcgacat cggcaaggtg tgggtcgcgg acgacggcgc
cgcggtggcg gtctggacca cgccggagg cgtcgaagcg
ggggcggtgt tcgccgagat cggccgcgc atggccgagt
tgagcggttc ccggctggcc gcgcagcaac agatggaagg
cctccggccg ccgcaccggc ccaaggagcc cgcgtggttc
ctggccaccg tcggcgtctc gcccgaccac cagggcaagg
gtctgggcag cgccgtcgtg ctccccggag tggaggcggc
cgagcgcgcc ggggtgcccg ccttcctgga gacctccgcg
ccccgcaacc tcccttcta cgagcggctc ggcttcaccg
tcaccgccga cgtcgagtgc ccgaaggacc gcgcgacctg
gtgcatgacc cgcaagcccg tgcctgagc ggccgcaatc
tagaccaaac ttgtttattg cagcttataa tggttacaaa
taaagcaata gcatcacaaa tttcacaaat aaagcatttt
tttcactgca ttctagttgt ggtttgtcca aactcatcaa
tgtatcttat catgtctgtg atcaggtacc aaagggcctc
gtgatacgcc tatttttata ggttaatgtc atgataataa
tggtttctta gacgtcaggt ggcactttc ggggaaatgt
gcgcggaacc cctatttgtt tatttttcta aatacattca
aatatgtatc cgctcatgag acaataaccc tgataaatgc
ttcaataata ttgaaaagg aagagtatga gtattcaaca
tttccgtgtc gcccttattc cctttttgc ggcattttgc
cttcctgttt ttgctcaccc agaaacgctg gtgaaagtaa
aagatgctga agatcagttg ggtgcacgag tgggttacat
cgaactggat ctcaacagcg gtaagatcct tgagagtttt
cgccccgaag aacgttttcc aatgatgagc actttaaag
ttctgctatg tggcgcggta ttatcccgta ttgacgccgg
gcaagagcaa ctcggtcgcc gcatacacta ttctcagaat
gacttggttg agtactcacc agtcacagaa aagcatctta
cggatggcat gacagtaaga gaattatgca gtgctgccat
aaccatgagt gataacactg cggccaactt acttctgaca
acgatcggag gaccgaagga gctaaccgct tttttgcaca
acatggggga tcatgtaact cgccttgatc gttgggaacc
ggagctgaat gaagccatac caaacgacga gcgtgacacc
acgatgcctg tagcaatggc aacaacgttg cgcaaactat
```

SEQUENCES

```
taactggcga actacttact ctagcttccc ggcaacaatt
aatagactgg atggaggcgg ataaagttgc aggaccactt
ctgcgctcgg cccttccggc tggctggttt attgctgata
aatctggagc cggtgagcgt gggtctcgcg gtatcattgc
agcactgggg ccagatggta agccctcccg tatcgtagtt
atctacacga cggggagtca ggcaactatg gatgaacgaa
atagacagat cgctgagata ggtgcctcac tgattaagca
ttggtaactg tcagaccaag tttactcata tactttag
attgatttaa aacttcattt ttaattaaaa agatctaggt
gaagatcctt tttgataatc tcatgaccaa aatcccttaa
cgtgagtttt cgttccactg agcgtcagac cccgtagaaa
agatcaaagg atcttcttga gatcctttt ttctgcgcgt
aatctgctgc ttgcaaacaa aaaaaccacc gctaccagcg
gtggtttgtt tgccggatca agagctacca actcttttc
cgaaggtaac tggcttcagc agagcgcaga taccaaatac
tgttcttcta gtgtagccgt agttaggcca ccacttcaag
aactctgtag caccgcctac atacctcgct ctgctaatcc
tgttaccagt ggctgctgcc agtggcgata agtcgtgtct
taccgggttg gactcaagac gatagttacc ggataaggcg
cagcggtcgg gctgaacggg gggttcgtgc acacagccca
gcttggagcg aacgacctac accgaactga gatacctaca
gcgtgagcta tgagaaagcg ccacgcttcc cgaagggaga
aaggcggaca ggtatccggt aagcggcagg gtcggaacag
gagagcgcac gagggagctt ccagggggaa acgcctggta
tctttatagt cctgtcgggt ttcgccacct ctgacttgag
cgtcgatttt tgtgatgctc gtcagggggg cggagcctat
ggaaaaacgc cagcaacgcg gcctttttac ggttcctggc
cttttgctgg ccttttgctc acatgttctt tcctgcgtta
tcccctgatt ctgtggataa ccgtattacc gcctttgagt
gagctgatac cgctcgccgc agccgaacga ccgagcgcag
cgagtcagtg agcgaggaag cggaagagcg cccaatacgc
aaaccgcctc tccccgcgcg ttggccgatt cattaatgca
gctggcacga caggtttccc gactggaaag cgggcagtga
gcgcaacgca attaatgtga gttagctc
```

SEQ ID NO: 4 -
```
tcgaggatcc tgacccatcc tgggcctcaa cttactcatc
ctgggaacgg gagacgattc acagaagaaa gcatgcaaga
gcagcgtcca ggctgaaaga actttgccaa cctggcactg
agaactgaat tccataggct gtgagctcta gcaatgccct
gtggactcag ttctggtgcc cggcagtgct acaacatcaa
tgccaaggcc gtgggcagc tgatggtttg ggctcccaac
ttcccagcca ggtgcttctg caggcccaca tcttgcccac
tgggctagct cga
```

---

What is claimed is:

1. A method comprising:
   harvesting exosomes containing miR-146b microRNA from a cell population of mesenchymal stem cells capable of producing exosomes containing miR-146b microRNA or media containing the cell population, confirming the presence of the miR-146b microRNA in the harvested exosomes; and
   administering the harvested exosomes to a subject suffering from a neuroinflammatory disease or injury in a pharmaceutically effective amount to treat the neuroinflammatory disease or injury in the subject.

2. The method of claim 1, wherein the exosomes are administered intravenously, nasally, intradermally, intraarterially, intraperitoneally, intralesionally, intracranially, intraarticularly, intraprostaticaly, intrapleurally, intratracheally, intravitreally, intravaginally, intrarectally, topically, intratumorally, intramuscularly, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, or stereotactically into neural tissue.

3. The method of claim 1, wherein the cell population is derived from the subject.

4. The method of claim 1, wherein the neuroinflammatory disease or injury comprises stroke, brain injury, central pontine, dementia, multiple sclerosis (MS) (together with the similar diseases called idiopathic inflammatory demyelinating diseases), tumefactive multiple sclerosis, Solitary sclerosis, Parkinson's disease, neuropathy, for example, peripheral neuropathy, Tabes Dorsalis, transverse myelitis, Devic's neuromyelitis optica, fulminant or acute idiopathic inflammatory-demyelinating disease, Marburg variant of multiple sclerosis, Balό's concentric sclerosis, Schilder's disease, acute disseminated encephalomyelitis; transverse myelitis, optic neuritis, progressive multifocal leukoencephalopathy, acute hemorrhagic leukoencephalitis, anti-myelin oligodendrocyte glycoprotein autoimmune encephalomyelitis, Leukodystrophy, adrenoleukodystrophy, chronic inflammatory demyelinating polyradiculoneuropathy (CIDP), Guillain-Barre syndrome, chronic inflammatory demyelinating polyneuropathy, or anti-MAG peripheral neuropathy.

5. The method of claim 4, wherein the neuroinflammatory disease or injury comprises dementia, peripheral neuropathy, stroke or multiple sclerosis.

6. A method comprising:
providing a cell population of mesenchymal stem cells capable of producing exosomes containing miR-146b; confirming the presence of the miR-146b microRNA in the cell population, and administering the cell population capable of producing exosomes containing miR-146b microRNA to a subject suffering from a neuroinflammatory disease or injury in a pharmaceutically effective amount to treat the neuroinflammatory disease or injury in the subject.

7. The method of claim 6, wherein the neurological neuroinflammatory disease or injury comprises stroke, brain injury, neonatal brain injury, central pontine, dementia, multiple sclerosis (MS) (together with the similar diseases called idiopathic inflammatory demyelinating diseases), tumefactive multiple sclerosis, Solitary sclerosis, Parkinson's disease, neuropathy, for example, peripheral neuropathy, Tabes *Dorsalis*, transverse myelitis, Devic's neuromyelitis optica, fulminant or acute idiopathic inflammatory-demyelinating disease, Marburg variant of multiple sclerosis, Balό's concentric sclerosis, Schilder's disease, acute disseminated encephalomyelitis; transverse myelitis, optic neuritis, progressive multifocal leukoencephalopathy, acute hemorrhagic leukoencephalitis, anti-(myelin oligodendrocyte glycoprotein) autoimmune encephalomyelitis, leukodystrophy, adrenoleukodystrophy, chronic inflammatory demyelinating polyradiculoneuropathy (CIDP), Guillain-Barre syndrome, chronic inflammatory demyelinating polyneuropathy, or anti-MAG peripheral neuropathy.

8. The method of claim 7, wherein the neurological disease neuroinflammatory disease or injury comprises dementia, peripheral neuropathy, stroke or multiple sclerosis.

9. A method comprising:
harvesting exosomes containing miR-146b microRNA from a cell population capable of producing the exosomes or media containing the cell population;
confirming the presence of the miR-146b microRNA in the harvested exosomes; and administering the harvested exosomes containing miR-146b microRNA to a subject suffering from stroke in a pharmaceutically effective amount to treat the stroke in the subject.

10. The method of claim 9, wherein the exosome producing cell population comprises: stem cells, mesenchymal stromal cells, umbilical cord cells, endothelial cells, Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia; or mastocytes.

11. The method of claim 9, wherein the exosomes are administered intravenously, nasally, intradermally, intraarterially, intraperitoneally, intralesionally, intracranially, intraarticularly, intraprostaticaly, intrapleurally, intratracheally, intravitreally, intravaginally, intrarectally, topically, intratumorally, intramuscularly, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, or directly into neural tissue.

12. A method comprising:
harvesting exosomes containing miR-146b microRNA from a cell population capable of producing exosomes containing miR-146b microRNA or media containing the cell population,
confirming the presence of the miR-146b microRNA in the harvested exosomes; and administering the harvested exosomes containing miR-146b microRNA to a subject suffering from dementia in a pharmaceutically effective amount to treat the subject with dementia.

13. The method of claim 12, wherein the cell population comprises: stem cells, mesenchymal stromal cells, umbilical cord cells, endothelial cells, Schwann cells, hematopoietic cells, reticulocytes, monocyte-derived dendritic cells (MDDCs), monocytes, B lymphocytes, antigen-presenting cells, glial cells, astrocytes, neurons, oligodendrocytes, spindle neurons, microglia; or mastocytes.

14. The method of claim 12, wherein the exosomes are administered intravenously, nasally, intradermally, intraarterially, intraperitoneally, intralesionally, intracranially, intraarticularly, intraprostaticaly, intrapleurally, intratracheally, intravitreally, intravaginally, intrarectally, topically, intratumorally, intramuscularly, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, or directly into neural tissue.

* * * * *

SEQUENCE LISTING

<160> NUMBER OF SEQ ID NOS: 4

<210> SEQ ID NO 1
<211> LENGTH: 4930
<212> TYPE: DNA
<213> ORGANISM: Artificial Sequence
<220> FEATURE:
<223> OTHER INFORMATION: pRNA-CMV3.1/Puro plasmid

<400> SEQUENCE: 1

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggag tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catggtgatg cggttttggc agtacatcaa tgggcgtgga tagcggtttg actcacgggg     420
atttccaagt ctccacccca ttgacgtcaa tgggagtttg ttttggcacc aaaatcaacg     480
```

-continued

```
ggactttcca aaatgtcgta acaactccgc cccattgacg caaatgggcg gtaggcgtgt      540
acggtgggag gtctatataa gcagagctgg tttagtgaac cgtggatccc gtcgcttacc      600
gattcagaat ggttgatatc cgccattctg aatcggtaag cgacgaagct taataaagga      660
tcttttattt tcattggatc tgtgtgttgg tttttttgtgt gcggccgccc tcgactgtgc     720
cttctagaag acaatagcag gcatgctggg gatgcggtgg gctctatggc ttctgaggcg      780
gaaagaacca gctggggctc taggggtat ccccacgcgc cctgtagcgg cgcattaagc      840
gcggcgggtg tggtggttac gcgcagcgtg accgctacac ttgccagcgc cctagcgccc      900 gctccttttcg ctttcttccc ttcctttctc gccacgttcg ccggctttcc ccgtcaagct     960
ctaaatcggg ggctcccttt agggttccga tttagtgctt tacggcacct cgaccccaaa    1020
aaacttgatt agggtgatgg ttcacgtagt gggccatcgc cctgatagac ggttttttcgc   1080 cctttgacgt tggagtccac gttctttaat agtggactct tgttccaaac tggaacaaca    1140 ctcaaccccta tctcggtcta ttcttttgat ttataaggga ttttgccgat tcggcctat    1200 tggttaaaaa atgagctgat ttaacaaaaa tttaacgcga attaattctg tggaatgtgt    1260
gtcagttagg gtgtggaaag tccccaggct ccccagcagg cagaagtatg caaagcatgc    1320
atctcaatta gtcagcaacc aggtgtggaa agtccccagg ctccccagca ggcagaagta    1380
tgcaaagcat gcatctcaat tagtcagcaa ccatagtccc gccccctaact ccgcccatcc    1440 cgcccctaac tccgcccagt tccgcccatt ctccgcccca tggctgacta atttttttta    1500
tttatgcaga ggccgaggcc gcctctgcct ctgagctatt ccagaagtag tgaggaggct    1560
tttttggagg cctaggcttt tgcaaaaagc tcccgggatg accgagtaca agcccacggt    1620
gcgcctcgcc accgcgacg acgtcccgcg ggcgtacgc accctcgccg ccgcgttcgc      1680
cgactacccc gccacgcgcc acaccgtcga cccggaccgc cacatcgagc gggtcaccga    1740
gctgcaagaa ctcttcctca cgcgcgtcgg gctcgacatc ggcaaggtgt gggtcgcgga   1800
cgacggcgcc gcggtggcgg tctggaccac gccggagagc gtcgaagcgg gggcggtgtt    1860
cgccgagatc ggcccgcgca tggccgagtt gagcggttcc cggctggccg cgcagcaaca    1920
gatggaaggc ctcctggcgc cgcaccggcc caaggagccc gcgtggttcc tggccaccgt   1980
cggcgtctcg cccgaccacc agggcaaggg tctgggcagc gccgtcgtgc tccccggagt    2040
ggaggcggcc gagcgcgccg gggtgccccgc cttcctggag acctccgcgc cccgcaacct    2100
ccccttctac gagcggctcg gcttcaccgt caccgccgac gtcgaggtgc ccgaaggacc    2160
gcgcacctgg tgcatgaccc gcaagcccgg tgcctgattc gaatgaccga ccaagcgacg    2220
cccaacctgc catcacgaga tttcgattcc accgccgcct tctatgaaag gttgggcttc    2280
ggaatcgttt tccgggacgc cggctggatg atcctccagc gcggggatct catgctggag    2340
ttcttcgccc accccaactt gtttattgca gcttataatg gttacaaata aagcaatagc    2400
atcacaaatt tcacaataa agcattttttt tcactgcatt ctagttgtgg tttgtccaaa    2460
ctcatcaatg tatcttatca tgtctgtata ccgtcgacct ctagctagag cttggcgtaa    2520
tcatggtcat agctgtttcc tgtgtgaaat tgttatccgc tcacaattcc acacaacata    2580
cgagccggaa gcataaagtg taaagcctgg ggtgcctaat gagtgagcta actcacatta    2640
attgcgttgc gctcactgcc cgctttccag tcgggaaacc tgtcgtgcca gctgcattaa    2700
tgaatcggcc aacgcgcggg gagaggcggt ttgcgtattg ggcgctcttc cgcttcctcg    2760
ctcactgact cgctgcgctc ggtcgttcgg ctgcggcgag cggtatcagc tcactcaaag    2820
```

| | |
|---|---|
| gcggtaatac ggttatccac agaatcaggg gataacgcag gaaagaacat gtgagcaaaa | 2880 |
| ggccagcaaa aggccaggaa ccgtaaaaag gccgcgttgc tggcgttttt ccataggctc | 2940 |
| cgccccctg acgagcatca aaaaatcga cgctcaagtc agaggtggcg aaacccgaca | 3000 |
| ggactataaa gataccaggc gtttccccct ggaagctccc tcgtgcgctc tcctgttccg | 3060 |
| accctgccgc ttaccggata cctgtccgcc tttctccctt cgggaagcgt ggcgctttct | 3120 |
| catagctcac gctgtaggta tctcagttcg gtgtaggtcg ttcgctccaa gctgggctgt | 3180 |
| gtgcacgaac cccccgttca gcccgaccgc tgcgccttat ccggtaacta tcgtcttgag | 3240 |
| tccaacccgg taagacacga cttatcgcca ctggcagcag ccactggtaa caggattagc | 3300 |
| agagcgaggt atgtaggcgg tgctacagag ttcttgaagt ggtggcctaa ctacggctac | 3360 |
| actagaagaa cagtatttgg tatctgcgct ctgctgaagc cagttacctt cggaaaaaga | 3420 |
| gttggtagct cttgatccgg caaacaaacc accgctggta gcggtttttt tgtttgcaag | 3480 |
| cagcagatta cgcgcagaaa aaaggatct caagaagatc ctttgatctt ttctacgggg | 3540 |
| tctgacgctc agtggaacga aaactcacgt taagggattt tggtcatgag attatcaaaa | 3600 |
| aggatcttca cctagatcct tttaaattaa aaatgaagtt ttaaatcaat ctaaagtata | 3660 |
| tatgagtaaa cttggtctga cagttaccaa tgcttaatca gtgaggcacc tatctcagcg | 3720 |
| atctgtctat ttcgttcatc catagttgcc tgactccccg tcgtgtagat aactacgata | 3780 |
| cgggagggct taccatctgg ccccagtgct gcaatgatac gcgagaccc acgctcaccg | 3840 |
| gctccagatt tatcagcaat aaaccagcca gccggaaggg ccgagcgcag aagtggtcct | 3900 |
| gcaactttat ccgcctccat ccagtctatt aattgttgcc gggaagctag agtaagtagt | 3960 |
| tcgccagtta atagtttgcg caacgttgtt gccattgcta caggcatcgt ggtgtcacgc | 4020 |
| tcgtcgtttg gtatggcttc attcagctcc ggttcccaac gatcaaggcg agttacatga | 4080 |
| tcccccatgt tgtgcaaaaa agcggttagc tccttcggtc ctccgatcgt tgtcagaagt | 4140 |
| aagttggccg cagtgttatc actcatggtt atggcagcac tgcataattc tcttactgtc | 4200 |
| atgccatccg taagatgctt ttctgtgact ggtgagtact caaccaagtc attctgagaa | 4260 |
| tagtgtatgc ggcgaccgag ttgctcttgc ccggcgtcaa tacgggataa taccgcgcca | 4320 |
| catagcagaa ctttaaaagt gctcatcatt ggaaaacgtt cttcggggcg aaaactctca | 4380 |
| aggatcttac cgctgttgag atccagttcg atgtaaccca ctcgtgcacc caactgatct | 4440 |
| tcagcatctt ttactttcac cagcgtttct gggtgagcaa aaacaggaag gcaaaatgcc | 4500 |
| gcaaaaaagg gaataaggc gacacggaaa tgttgaatac tcatactctt ccttttcaa | 4560 |
| tattattgaa gcatttatca gggttattgt ctcatgagcg gatacatatt tgaatgtatt | 4620 |
| tagaaaaata aacaaatagg ggttccgcgc acatttcccc gaaaagtgcc acctgacgtc | 4680 |
| gacggatcgg gagatctccc gatcccctat ggtgcactct cagtacaatc tgctctgatg | 4740 |
| ccgcatagtt aagccagtat ctgctccctg cttgtgtgtt ggaggtcgct gagtagtgcg | 4800 |
| cgagcaaaat ttaagctaca acaaggcaag gcttgaccga caattgcatg aagaatctgc | 4860 |
| ttagggttag gcgttttgcg ctgcttcgcg atgtacgggc cagatatacg cgttgacatt | 4920 |
| gattattgac | 4930 |

```
<210> SEQ ID NO 2
<211> LENGTH: 72
<212> TYPE: DNA
<213> ORGANISM: Caenorhabditis elegans
<220> FEATURE:
<221> NAME/KEY: misc_feature
```

```
<222> LOCATION: (1)..(72)
<223> OTHER INFORMATION: C.elegans miR-67

<400> SEQUENCE: 2
ggatcctcac aacctcctag aaagagtaga ttgatatccg tctactcttt ctaggaggtt    60
gtgacgaagc tt                                                       72

<210> SEQ ID NO 3
<211> LENGTH: 5268
<212> TYPE: DNA
<213> ORGANISM: Artificial Sequence
<220> FEATURE:
<223> OTHER INFORMATION: pEP-miR plasmid
<220> FEATURE:
<221> NAME/KEY: misc_feature
<222> LOCATION: (1307)..(1406)
<223> OTHER INFORMATION: n is a, c, g, t or u

<400> SEQUENCE: 3
cccaactttt aaaagaaaag gggggattgg ggggtacagt gcaggggaaa gaatagtaga     60
cataatagca acagacatac aaactaaaga attacaaaaa caaattacaa aattcaaaat    120
tttatcgatg cctccccgtc caccccccc ccaacccgcc ccgaccggag ctgagagtaa    180
ttcatacaaa aggactcgcc cctgccttgg ggaatcccag ggaccgtcgt taaactccca    240
ctaacgtaga acccagagat cgctgcgttc ccgcccctc acccgcccgc tctcgtcatc    300
actgaggtgg agaagagcat gcgtgaggct ccggtgcccg tcagtgggca gagcgcacat    360
cgcccacagt ccccgagaag ttgggggggag gggtcggcaa ttgaaccggt gcctagagaa    420
ggtggcgcgg ggtaaactgg gaaagtgatg tcgtgtactg gctccgcctt tttcccgagg    480 gtggggggaga accgtatata agtgcagtag tcgccgtgaa cgttcttttt cgcaacgggt    540
ttgccgccag aacacaggta agtgccgtgt gtggttcccg cgggcctggc ctctttacgg    600
gttatggccc ttgcgtgcct tgaattactt ccacgcccct ggctgcagta cgtgattctt    660
gatcccgagc ttcggggttgg aagtgggtgg gagagttcga ggccttgcgc ttaaggagcc    720
ccttcgcctc gtgcttgagt tgaggcctgg cctgggcgct ggggccgccg cgtgcgaatc    780
tggtggcacc ttcgcgcctg tctcgctgct ttcgataagt ctctagccat ttaaaatttt    840
tgatgatatc ctgcgacgct ttttttctgg caagatagtc ttgtaaatgc gggccaagat    900
ctgcacactg gtatttcggt ttttgggggcc gcggcggcg acggggcccg tgcgtcccag    960
cgcacatgtt cggcgaggcg gggcctgcga gcgcggccac cgagaatcgg acggggtag   1020 tctcaagctg gccggcctgc tctggtgcct ggcctcgcgc cgccgtgtat cgccccgccc   1080
tgggcggcaa ggctggcccg gtcggcacca gttgcgtgag cggaaagatg gccgcttccc   1140
ggccctgctg cagggagctc aaaatggagg acgcggcgct cggagagcg ggcgggtgag   1200 tcacccacac aaaggaaaag ggcctttccg tcctcagccg tcgcttcatg tgactccacg   1260
gagtaccggg cgccgtccag gcacctcgat tagttctcga ggatccnnnn nnnnnnnnn   1320 nnnnnnnnnn nnnnnnnnnn nnnnnnnnnn nnnnnnnnnn nnnnnnnnnn nnnnnnnnnn   1380
nnnnnnnnnn nnnnnnnnnn nnnnngcta gctcgagctt ttggagtacg tcgtctttag   1440
gttgggggga gggttttat gcgatggagt ttccccacac tgagtgggtg gagactgaag   1500
ttaggccagc ttggcacttg atgtaattct ccttggaatt tgccctttt gagtttggat   1560 cttggttcat tctcaagcct cagacagtgg ttcaaagtttt tttcttcca tttcaggtgt   1620 cgtgaaaact accccctctag agtcgagcta ccggtcgcca ccatggtgag caagggcgag   1680
```

```
gaggataaca tggccatcat caaggagttc atgcgcttca aggtgcacat ggagggctcc   1740
gtgaacggcc acgagttcga gatcgagggc gagggcgagg ccgcccccta cgagggcacc   1800
cagaccgcca agctgaaggt gaccaagggt ggcccctgc ccttcgcctg ggacatcctg    1860
tcccctcagt tcatgtacgg ctccaaggcc tacgtgaagc accccgccga catccccgac   1920
tacttgaagc tgtccttccc cgagggcttc aagtgggagc gcgtgatgaa cttcgaggac   1980
ggcggcgtgg tgaccgtgac ccaggactcc tccctgcagg acggcgagtt catctacaag   2040
gtgaagctgc gcggcaccaa cttccctcc gacggccccg taatgcagaa gaagaccatg    2100
ggctgggagg cctcctccga gcggatgtac cccgaggacg gcgccctgaa gggcgagatc   2160
aagcagaggc tgaagctgaa ggacggcggc cactacgacg ctgaggtcaa gaccacctac   2220
aaggccaaga gcccgtgca gctgcccggc gcctacaacg tcaacatcaa gttggacatc    2280
acctcccaca acgaggacta caccatcgtg aacagtacg aacgcgccga gggccgccac    2340
tccaccggcg gcatggacga gctgtacaag gacccaccgg tcgccaccat gaccgagtac   2400
aagcccacgg tgcgcctcgc cacccgcgac gacgtcccca gggccgtacg cacctcgcc    2460
gccgcgttcg ccgactaccc cgccacgcgc cacaccgtcg atccggaccg ccacatcgag   2520
cgggtcaccg agctgcaaga actcttcctc acgcgcgtcg ggctcgacat cggcaaggtg   2580
tgggtcgcgg acgacggcgc cgcggtggcg gtctggacca cgccggagag cgtcgaagcg   2640
ggggcggtgt cgccgagat cggcccgcgc atggccgagt tgagcggttc ccggctggcc    2700
gcgcagcaac agatggaagg cctcctggcg ccgcaccggc ccaaggagcc cgcgtggttc   2760
ctggccaccg tcgcgtctc gcccgaccac cagggcaagg tctgggcag cgccgtcgtg     2820
ctccccggag tggaggcggc cgagcgcgcc ggggtgcccg ccttcctgga gacctccgcg   2880
ccccgcaacc tccccttcta cgagcggctc ggcttcaccg tcaccgccga cgtcgagtgc   2940
ccgaaggacc gcgcgacctg gtgcatgacc cgcaagcccg gtgcctgagc ggccgcaatc   3000
tagaccaaac ttgtttattg cagcttataa tggttacaaa taaagcaata gcatcacaaa   3060
tttcacaaat aaagcatttt tttcactgca ttctagttgt ggtttgtcca aactcatcaa   3120
tgtatcttat catgtctgtg atcaggtacc aaagggcctc gtgatacgcc tatttttata   3180
ggttaatgtc atgataataa tggtttctta gacgtcaggt ggcactttc ggggaaatgt    3240
gcgcggaacc cctatttgtt tatttttcta aatacattca aatatgtatc cgctcatgag   3300
acaataaccc tgataaatgc ttcaataata ttgaaaaagg aagagtatga gtattcaaca   3360
tttccgtgtc gcccttattc cctttttgc ggcattttgc cttcctgttt ttgctcaccc    3420
agaaacgctg gtgaaagtaa aagatgctga agatcagttg ggtgcacgag tgggttacat   3480
cgaactggat ctcaacagcg gtaagatcct tgagagtttt cgccccgaag aacgttttcc   3540
aatgatgagc acttttaaag ttctgctatg tggcgcggta ttatcccgta ttgacgccgg   3600
gcaagagcaa ctcggtcgcc gcatacacta ttctcagaat gacttggttg agtactcacc   3660
agtcacagaa aagcatctta cggatggcat gacagtaaga gaattatgca gtgctgccat   3720
aaccatgagt gataacactg cggccaactt acttctgaca acgatcggag gaccgaagga   3780
gctaaccgct tttttgcaca acatggggga tcatgtaact cgccttgatc gttgggaacc   3840
ggagctgaat gaagccatac caaacgacga gcgtgacacc acgatgcctg tagcaatggc   3900
aacaacgttg cgcaaactat taactggcga actacttact ctagcttccc ggcaacaatt   3960
aatagactgg atggaggcgg ataaagttgc aggaccactt ctgcgctcgg cccttccggc   4020
tggctggttt attgctgata aatctggagc cggtgagcgt gggtctcgcg gtatcattgc   4080
```

```
                                              -continued
agcactgggg ccagatggta agccctcccg tatcgtagtt atctacacga cggggagtca    4140
ggcaactatg gatgaacgaa atagacagat cgctgagata ggtgcctcac tgattaagca    4200
ttggtaactg tcagaccaag tttactcata tatactttag attgatttaa aacttcattt    4260
ttaattaaaa agatctaggt gaagatcctt tttgataatc tcatgaccaa aatcccttaa    4320
cgtgagtttt cgttccactg agcgtcagac cccgtagaaa agatcaaagg atcttcttga    4380
gatccttttt ttctgcgcgt aatctgctgc ttgcaaacaa aaaaaccacc gctaccagcg    4440
gtggtttgtt tgccggatca agagctacca actcttttc cgaaggtaac tggcttcagc     4500
agagcgcaga taccaaatac tgttcttcta gtgtagccgt agttaggcca ccacttcaag    4560
aactctgtag caccgcctac atacctcgct ctgctaatcc tgttaccagt ggctgctgcc    4620
agtggcgata agtcgtgtct taccgggttg gactcaagac gatagttacc ggataaggcg    4680
cagcggtcgg gctgaacggg gggttcgtgc acacagccca gcttggagcg aacgacctac    4740
accgaactga gatacctaca gcgtgagcta tgagaaagcg ccacgcttcc cgaagggaga    4800
aaggcggaca ggtatccggt aagcggcagg gtcggaacag gagagcgcac gagggagctt    4860
ccagggggaa acgcctggta tctttatagt cctgtcgggt ttcgccacct ctgacttgag    4920
cgtcgatttt tgtgatgctc gtcaggggg cggagcctat ggaaaaacgc cagcaacgcg    4980 gccttttac ggttcctggc cttttgctgg ccttttgctc acatgttctt tcctgcgtta     5040
tcccctgatt ctgtggataa ccgtattacc gcctttgagt gagctgatac cgctcgccgc    5100
agccgaacga ccgagcgcag cgagtcagtg agcgaggaag cggaagagcg cccaatacgc    5160
aaaccgcctc tccccgcgcg ttggccgatt cattaatgca gctggcacga caggtttccc    5220
gactggaaag cgggcagtga gcgcaacgca attaatgtga gttagctc                5268

<210> SEQ ID NO 4
<211> LENGTH: 293
<212> TYPE: DNA
<213> ORGANISM: Homo sapiens
<220> FEATURE:
<221> NAME/KEY: misc_feature
<222> LOCATION: (1)..(293)
<223> OTHER INFORMATION: Human miR-146b

<400> SEQUENCE: 4
tcgaggatcc tgacccatcc tgggcctcaa cttactcatc ctgggaacgg gagacgattc      60
acagaagaaa gcatgcaaga gcagcgtcca ggctgaaaga actttggcca cctggcactg     120
agaactgaat tccataggct gtgagctcta gcaatgccct gtggactcag ttctggtgcc     180
cggcagtgct acaacatcaa tgccaaggcc gtggggcagc tgatggtttg ggctcccaac    240
ttcccagcca ggtgcttctg caggcccaca tcttgcccac tgggctagct cga           293
```